United States Patent
Deisseroth et al.

(10) Patent No.: US 10,252,076 B2
(45) Date of Patent: *Apr. 9, 2019

(54) UPCONVERSION OF LIGHT FOR USE IN OPTOGENETIC METHODS

(71) Applicant: The Board of Trustees of the Leland Stanford Junior University, Stanford, CA (US)

(72) Inventors: Karl Deisseroth, Stanford, CA (US); Polina Anikeeva, Somerville, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/214,403

(22) Filed: Jul. 19, 2016

(65) Prior Publication Data

US 2016/0317658 A1    Nov. 3, 2016

Related U.S. Application Data

(63) Continuation of application No. 13/882,703, filed as application No. PCT/US2011/059287 on Nov. 4, 2011, now Pat. No. 9,522,288.

(60) Provisional application No. 61/410,729, filed on Nov. 5, 2010.

(51) Int. Cl.
| | | |
|---|---|---|
| *A61D 7/00* | (2006.01) | |
| *A61K 38/17* | (2006.01) | |
| *A61N 5/06* | (2006.01) | |
| *A61K 41/00* | (2006.01) | |
| *B82Y 5/00* | (2011.01) | |
| *A61K 48/00* | (2006.01) | |
| *A61K 9/00* | (2006.01) | |
| *A61K 9/16* | (2006.01) | |
| *C12N 7/00* | (2006.01) | |

(52) U.S. Cl.
CPC .............. *A61N 5/0613* (2013.01); *A61D 7/00* (2013.01); *A61K 9/0019* (2013.01); *A61K 9/1611* (2013.01); *A61K 38/177* (2013.01); *A61K 41/00* (2013.01); *A61K 41/008* (2013.01); *A61K 41/0038* (2013.01); *A61K 48/0083* (2013.01); *A61N 5/062* (2013.01); *A61N 5/0622* (2013.01); *B82Y 5/00* (2013.01); *C12N 7/00* (2013.01); *A61N 2005/0659* (2013.01); *A61N 2005/0662* (2013.01); *A61N 2005/0663* (2013.01); *C12N 2750/14143* (2013.01)

(58) Field of Classification Search
CPC ............ A61K 41/00; A61K 41/0038; A61K 48/0083; A61N 2005/0659; A61N 2005/0662; A61N 5/0613; A61N 5/062; A61N 5/0622; B82Y 5/00

USPC ........................................................ 607/100
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |

(Continued)

FOREIGN PATENT DOCUMENTS

| | | |
|---|---|---|
| CN | 1079464 A | 12/1993 |
| CN | 1558222 A | 12/2004 |

(Continued)

OTHER PUBLICATIONS

Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).

(Continued)

*Primary Examiner* — Janet L Epps-Smith
(74) *Attorney, Agent, or Firm* — Rudy J. Ng; Paula A. Borden; Bozicevic, Field & Francis LLP

(57) ABSTRACT

Provided herein are compositions comprising lanthanide-doped nanoparticles which upconvert electromagnetic radiation from infrared or near infrared wavelengths into the visible light spectrum. Also provided herein are methods activating light-responsive opsin proteins expressed on plasma membranes of neurons and selectively altering the membrane polarization state of the neurons using the light delivered by the lanthanide-doped nanoparticles.

28 Claims, 2 Drawing Sheets
Specification includes a Sequence Listing.

(56) References Cited

U.S. PATENT DOCUMENTS

| | | |
|---|---|---|
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Deisseroth et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,284,353 B2 | 3/2016 | Deisseroth et al. |
| 9,308,392 B2 | 4/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,421,258 B2 | 8/2016 | Deisseroth et al. |
| 9,522,288 B2 * | 12/2016 | Deisseroth et al. .. A61N 5/0613 607/100 |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |

(56) References Cited

U.S. PATENT DOCUMENTS

| | | |
|---|---|---|
| 2005/0102708 A1 | 5/2005 | Lecanu et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0209352 A1* | 8/2010 | Hultman et al. ................ 424/9.3 |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0089503 A1 | 4/2013 | Deisseroth et al. |
| 2013/0144359 A1 | 6/2013 | Kishawi et al. |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0072394 A1 | 3/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2015/0297719 A1 | 10/2015 | Deisseroth et al. |
| 2016/0002302 A1 | 1/2016 | Deisseroth et al. |
| 2016/0015996 A1 | 1/2016 | Deisseroth et al. |
| 2016/0038761 A1 | 2/2016 | Deisseroth et al. |
| 2016/0038764 A1 | 2/2016 | Deisseroth et al. |
| 2016/0045599 A1 | 2/2016 | Deisseroth et al. |

(56) References Cited

U.S. PATENT DOCUMENTS

| | | | |
|---|---|---|---|
| 2016/0096036 A1 | 4/2016 | Deisseroth et al. | |
| 2016/0175607 A1 | 6/2016 | Deisseroth et al. | |

FOREIGN PATENT DOCUMENTS

| | | | | |
|---|---|---|---|---|
| CN | 101288768 | A | 10/2008 | |
| CN | 102076866 | A | 5/2011 | |
| CN | 103313752 | A | 9/2013 | |
| CN | 103476456 | A | 12/2013 | |
| EP | 1197144 | | 4/2002 | |
| EP | 1334748 | | 8/2003 | |
| EP | 1444889 | | 8/2004 | |
| EP | 1873566 | | 1/2008 | |
| JP | 6295350 | | 10/1994 | |
| JP | H 09505771 | A | 6/1997 | |
| JP | 2004534508 | | 11/2004 | |
| JP | 2005034073 | A | 2/2005 | |
| JP | 2006217866 | | 8/2006 | |
| JP | 2007530027 | A | 11/2007 | |
| JP | 2008010422 | A | 1/2008 | |
| JP | 2010227537 | A | 10/2010 | |
| JP | 2012508581 | | 4/2012 | |
| WO | WO 1995/005214 | | 2/1995 | |
| WO | WO 1996/032076 | | 10/1996 | |
| WO | WO 2000/027293 | | 5/2000 | |
| WO | WO 2001/025466 | | 4/2001 | |
| WO | WO 2003/016486 | | 2/2003 | |
| WO | WO 2003/040323 | | 5/2003 | |
| WO | W0 2003/046141 | | 6/2003 | |
| WO | WO 2003/046141 | | 6/2003 | |
| WO | WO 2003/084994 | | 10/2003 | |
| WO | WO 2003/102156 | | 12/2003 | |
| WO | WO 2004/033647 | | 4/2004 | |
| WO | WO 2005/093429 | | 10/2005 | |
| WO | WO 2006/103678 | | 10/2006 | |
| WO | WO 2007/024391 | | 3/2007 | |
| WO | WO 2007/131180 | | 11/2007 | |
| WO | WO 2008/014382 | | 1/2008 | |
| WO | WO-2008014382 | A2 * | 1/2008 | ........... C07K 14/705 |
| WO | WO 2008/086470 | | 7/2008 | |
| WO | WO 2008/106694 | | 9/2008 | |
| WO | WO 2009/025819 | | 2/2009 | |
| WO | WO 2009/072123 | | 6/2009 | |
| WO | WO 2009/119782 | | 10/2009 | |
| WO | WO 2009/131837 | | 10/2009 | |
| WO | WO 2009/148946 | | 12/2009 | |
| WO | WO 2010/006049 | | 1/2010 | |
| WO | WO 2010/011404 | | 1/2010 | |
| WO | WO 2010/056970 | | 5/2010 | |
| WO | WO 2010/123993 | | 10/2010 | |
| WO | WO 2010/123993 | A1 * | 1/2010 | ......... A61K 49/0039 |
| WO | WO 2011/005978 | | 1/2011 | |
| WO | WO 2011/066320 | | 6/2011 | |
| WO | WO 2011/106783 | | 9/2011 | |
| WO | WO 2011/116238 | | 9/2011 | |
| WO | WO 2011/127088 | | 10/2011 | |
| WO | WO 2012/032103 | | 3/2012 | |
| WO | WO 2012/061676 | | 5/2012 | |
| WO | WO 2012/061681 | | 5/2012 | |
| WO | WO 2012/061684 | | 5/2012 | |
| WO | WO 2012/061688 | | 5/2012 | |
| WO | WO 2012/061690 | | 5/2012 | |
| WO | WO 2012/061741 | | 5/2012 | |
| WO | WO 2012/061744 | | 5/2012 | |
| WO | WO 2012/106407 | | 8/2012 | |
| WO | WO 2012/134704 | | 10/2012 | |
| WO | WO 2013/003557 | | 1/2013 | |
| WO | WO 2013/016486 | | 1/2013 | |
| WO | WO 2013/090356 | | 6/2013 | |
| WO | WO 2013/126521 | | 8/2013 | |
| WO | WO 2013/126762 | | 8/2013 | |
| WO | WO 2013/142196 | | 9/2013 | |
| WO | WO 2014/081449 | | 5/2014 | |
| WO | WO 2014/117079 | | 7/2014 | |
| WO | WO 2016/019075 | | 2/2016 | |

OTHER PUBLICATIONS

Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).

Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.

Aebischer, et al. "Long-Term Cross-Species Brain Transplantation of a Polymer-Encapsulated Dopamine-Secreting Cell Line", Experimental Neurology, 1991, vol. 111, pp. 269-275.

Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.

Ahmad, et al. "The *Drosophila rhodopsin* cytoplasmic tail domain is required for maintenance of rhabdomere structure." The FASEB Journal, 2007, vol. 21, p. 449-455.

Airan, et al.; "Integration of light-controlled neuronal firing and fast circuit imaging"; Current Opinion in Neurobiology; vol. 17, pp. 587-592 (2007).

Airan, et al., "Temporally Precise in vivo Control of Intracellular Signaling", 2009, Nature, vol. 458, No. 7241, pp. 1025-1029.

Akirav, et al. "The role of the medial prefrontal cortex-amygdala circuit in stress effects on the extinction of fear", Neural Plasticity, 2007: vol. 2007 Article ID:30873, pp. 1-11.

Ali; "Gene and stem cell therapy for retinal disorders"; vision-research.en—The Gateway to European Vision Research; accessed from http://www.vision-research.eu/index.php?id=696, 10 pages. (accessed Jul. 24, 2015).

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the cre Gene Mediated by Cre Recombinase Using a Combination of Mutant lox Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.

Arenkiel, et al. "In vivo light-induced activation of neural circuitry in transgenic mice expressing Channelrhodopsin-2", Neuron, 2007, 54:205-218.

Argos, et al. "The integrase family of site-specific recombinases: regional similarities and global diversity", The EMBO Journal, 1986, vol. 5, No. 2, pp. 433-440.

Asano, et al.; "Optically Controlled Contraction of Photosensitive Skeletal Muscle Cells"; Biotechnology & Bioengineering; vol. 109, No. 1, pp. 199-204 (Jan. 2012).

Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.

Babin et al., "Zebrafish Models of Human Motor Neuron Diseases: Advantages and Limitations", Progress in Neurobiology (2014), 118:36-58.

Balint et al., "The Nitrate Transporting Photochemical Reaction Cycle of the Pharanois Halorhodopsin", Biophysical Journal, 2004, 86:1655-1663.

Bamberg et al. "Light-driven proton or chloride pumping by halorhodopsin." Proc. Natl. Academy Science USA, 1993, vol. 90, No. 2, p. 639-643.

Banghart, et al. "Light-activated ion channels for remote control of neuronal firing". Nature Neuroscience, 2004, vol. 7, No. 12 pp. 1381-1386.

Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).

Basil et al., "Is There Evidence for Effectiveness of Transcranial Magnetic Stimulation in the Treatment of Psychiatric Disorders?"; Psychiatry; vol. 1, No. 11, pp. 64-69 (Nov. 2005).

(56) References Cited

OTHER PUBLICATIONS

Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga *Volvox carteri*", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.

Campagnola et al. "Fiber-coupled light-emitting diode for localized photostimulation of neurons expressing channelrhodopsin-2." Journal of Neuroscience Methods , 2008, vol. 169, Issue 1. Abstract only.
Cannon, et al.; "Endophenotypes in the Genetic Analyses of Mental Disorders"; Annu. Rev. Clin. Psychol.; vol. 2, pp. 267-290 (2006).
Cardin, et al. "Driving Fast spiking Cells Induces Gamma Rhythm and Controls Sensory Responses", 2009, Nature, vol. 459, vol. 7247, pp. 663-667.
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Chow et al., "Optogenetics and translation medicine", Sci Transl Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. " Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).

(56) References Cited

OTHER PUBLICATIONS

Dederen, et al. "Retrograde neuronal tracing with cholera toxin B subunit: comparison of three different visualization methods", Histochemical Journal, 1994, vol. 26, pp. 856-862.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Deonarain; "Ligand-targeted receptor-mediated vectors for gene delivery"; Exp. Opin. Ther. Patents; vol. 8, No. 1, pp. 53-69 (1998).
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "N. pharaonis halorhodopsin (hop) gene, complete cds"; (Nov. 22, 1990).
EBI accession No. UNIPROT: A7U0Y6; "SubName: Full= Bacteriorhodopsin"; (Aug. 10, 2010).
EBI accession No. UNIPROT: B0R5N9; "Subname: Full= Bacteriorhodopsin"; (Apr. 8, 2008).
EBI accession No. UNIPROT: B4Y103; "SubName: Full= Channelrhodopsin-1"; (Sep. 23, 2008).
EBI accession No. UNIPROT: P15647; "RecName: Full= Halorhodopsin; Short=HR; Alt Name: Full=NpHR"; (Apr. 1, 1990).
Edelstein, et al.; "Gene therapy clinical trials worldwide 1989-2004—an overview"; The Journal of Gene Medicine; vol. 6, pp. 597-602 (2004).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain" , Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine D2 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.

(56) References Cited

OTHER PUBLICATIONS

Gorelova et al., "The course of neural projection from the prefrontal cortex to the nucleus accumbens in the rat", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet., 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Grady, et al.; "Age-Related Reductions in Human Recognition Memory Due to Impaired Encoding"; Science; vol. 269, No. 5221, pp. 218-221 (Jul. 14, 1995).
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol., 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $β_2$m: an animal model of HLA-B27-associated human disorders", Cell, 1990, vol. 63, pp. 1099-1112.
Han, et al.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.

Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J., 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylcholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane," PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers" Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; VOI. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.

(56) References Cited

OTHER PUBLICATIONS

Jimenez S.A & Maren S. et al/ "Nuclear disconnection within the amygdala reveals a direct pathway to fear", Learning Memory, 2009, vol. 16: pp. 766-768.

Johansen, et al., "Optical Activation of Lateral Amygdala Pyramidal Cells Instructs Associative Fear Learning", 2010, PNAS, vol. 107, No. 28, pp. 12692-12697.

Johnson-Saliba, et al.; "Gene Therapy: Optimising DNA Delivery to the Nucleus"; Current Drug Targets; vol. 2, pp. 371-399 (2001).

Johnston et al. "Isolation of the yeast regulatory gene GAL4 and analysis of its dosage effects on the galactose/melibiose regulon," PNAS, 1982, vol. 79, pp. 6971-6975.

Jones, et al.; "Animal Models of Schizophrenia"; British Journal of Pharmacology; vol. 164, pp. 1162-1194 (2011).

Kaiser; "Clinical research. Death prompts a review of gene therapy vector"; Science; 317(5838):580, 1 page (Aug. 3, 2007).

Kandel, E.R.,et al. "Electrophysiology of Hippocampal Neurons: I. Sequential Invasion and Synaptic Organization," J Neurophysiol, 1961, vol. 24, pp. 225-242.

Kandel, E.R.,et al. "Electrophysiology of Hippocampal Neurons: II. After-Potentials and Repetitive Firing", J Neurophysiol., 1961, vol. 24, pp. 243-259.

Karra, et al. "Transfection Techniques for Neuronal Cells", The Journal of Neuroscience, 2010, vol. 30, No. 18, pp. 6171-6177.

Karreman et al. "On the use of double FLP recognition targets (FRTs) in the LTR of retroviruses for the construction of high producer cell lines" , Nucleic Acids Research, 1996, vol. 24, No. 9: pp. 1616-1624.

Kato et al. "Present and future status of noninvasive selective deep heating using RF in hyperthermia." Med & Biol. Eng. & Comput 31 Supp: S2-11, 1993. Abstract. p. S2 only.

Katz, et al. "Scanning laser photostimulation: a new approach for analyzing brain circuits," Journal of Neuroscience Methods, 1994, vol. 54, pp. 205-218.

Kay; "State-of-the-art gene-based therapies: the road ahead"; Nature Reviews Genetics; vol. 12, pp. 316-328 (May 2011).

Kelder et al., "Glycoconjugates in human and transgenic animal milk", Advances in Exp. Med. And Biol., 2001, vol. 501, pp. 269-278.

Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).

Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.

Khosravani et al., "Voltage-Gated Calcium Channels and Idiopathic Generalized Epilepsies", Physiol. Rev., 2006, vol. 86: pp. 941-966.

Kianianmomeni, et al. "Channelrhodopsins of Volvox cartei are Photochromic Proteins that are Specifically Expressed in Somatic Cells under Control of Light, Temperature, and the Sex Inducer", 2009, Plant Physiology, vol. 151, No. 1, pp. 347-366.

Kim et al., "Diverging neural pathways assemble a behavioural state from separable features in anxiety" Nature, 2013, 496(7444):219-23.

Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.

Kim et al., "PDZ domain proteins of synapses", Nature Reviews Neuroscience, 2004, vol. 5, No. 10, pp. 771-781.

Kingston et al. "Transfection and Expression of Cloned DNA," Supplement 31, Current Protocols in Immunology, 1999, 10.13.1-1 0.13.9.

Kingston et al. "Transfection of DNA into Eukaryotic Cells," Supplement 63, Current Protocols in Molecular Biology, 1996, 9.1.1-9.1.11, 11 pages.

Kinoshita, et al., "Optogenetically Induced Supression of Neural Activity in the Macaque Motor Cortex", Poster Sessions Somatomotor System, Others, Society for Neuroscience Meeting, 2010, pp. 141-154.

Kita, H. et al. "Effects of dopamine agonists and antagonists on optical responses evoked in rat frontal cortex slices after stimulation of the subcortical white matter," Exp. Brain Research, 1999, vol. 125, pp. 383-388.

Kitabatake et al., "Impairment of reward-related learning by cholinergic cell ablationn in the striatum", PNAS, Jun. 2003, 100(13):7965-7970.

Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.

Klausberger, et al. "Brain-state- and cell-type-specific firing of hippocampal interneurons in vivo", Nature, 2003, vol. 421: pp. 844-848.

Knopfel, et al. "Optical Probing of Neuronal Circuit Dynamics: Gentically Encoded Versus Classical Fluorescent Sensors", 2006, Trends Neurosci, vol. 29, No. 3, pp. 160-166.

Knopfel, et al.; "A comprehensive concept of optogenetics"; Progress in Brain Research; vol. 196, pp. 1-28 (2012).

Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.

Kokel et al., "Photochemical activation of TRPA1 channels in neurons and animals", Nat Chem Biol, 2013, 9(4):257-263.

Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.

Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.

Lalumiere, R., "A new technique for controlling the brain: optogenetics and its potential for use in research and the clinic", Brain Stimulation, 2011, vol. 4, pp. 1-6.

Lammel et al., "Input-specific control of reward and aversion in the ventral tegmental area", Nature, 2012, 491(7423):212-217.

Landy, A. "Mechanistic and structural complexity in the site-specific recombination pathways of Int and FLP", Current Opinion in Genetics and Development, 1993, vol. 3, pp. 699-707.

Lanyi et al. "The primary structure of a Halorhodopsin from Natronobacterium Pharaonis" Journal of Biological Chemistry, 1990, vol. 265, No. 3, p. 1253-1260.

Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.

Lee et al., "Potassium Channel Gene Therapy Can Prevent Neuron Death Resulting from Necrotic and Apoptotic Insults", Journal of Neurochemistry, 2003, vol. 85: pp. 1079-1088.

Levitan et al. "Surface Expression of Kv1 Voltage-Gated K+ Channels Is Governed by a C-terminal Motif," Trends Cardiovasc. Med., 2000, vol. 10, No. 7, pp. 317-320.

Li et al. "Fast noninvasive activation and inhibition of neural and network activity by vertebrate rhodopsin and green algae channelrhodopsin." PNAS, 2005, vol. 102, No. 49, p. 17816-17821.

Li et al., "Surface Expression of Kv1 Channels is Governed by a C-Terminal Motif", J. Bioi. Chem. (2000), 275(16):11597-11602.

Lim et al., "A Novel Targeting Signal for Proximal Clustering of the Kv2.1K+ Channel in Hippocampal Neurons", Neuron, 2000, vol. 25: pp. 385-397.

Lima, et al. "Remote Control of Behavior through Genetically Targeted Photostimulation of Neurons", Cell, 2005, vol. 121: pp. 141-152.

Liman, et al. "Subunit Stoichiometry of a Mammalian K+ Channel Determined by Construction of Multimeric cDNAs," Neuron, 1992,vol. 9, pp. 861-871.

(56) References Cited

OTHER PUBLICATIONS

Lin, "A user's guide to channelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
Mcallister, "Cellular and Molecular Mechanisms of Dendrite Growth", 2000, Cereb Cortex, vol. 10, No. 10, pp. 963-973.
Mcknight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging, 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.

Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Palu, et al.; "In pursuit of new developments for gene therapy of human diseases"; Journal of Biotechnology; vol. 68, pp. 1-13 (1999).

(56) References Cited

OTHER PUBLICATIONS

Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. " Illumination of the Melanopsin Signaling Pathway", Science, 2005, vol. 307: pp. 600-604.
Pandya, et al.; "Where in the Brain is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1-9.1 1 .1 8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Pfeifer, et al.; "Gene Therapy: Promises and Problems"; Annu. Rev. Genomics Hum. Genet.; vol. 2, pp. 177-211 (2001).
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Powell, et al.; "Schizophrenia-Relevant Behavioral Testing in Rodent Models: A Uniquely Human Disorder?"; Biol. Psychiatry; vol. 59, pp. 1198-1207 (2006).
Qiu et al. "Induction of photosensitivity by heterologous expression of melanopsin", Nature, 2005, vol. 433: pp. 745-749.
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).

Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Schroll et al., "Light-induced activation of distinct modulatory neurons triggers appetitive or aversive learning in *Drosophila* larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.

(56) References Cited

OTHER PUBLICATIONS

Shoji, et al.; "Current Status of Delivery Systems to Improve Target Efficacy of Oligonucleotides"; Current Pharmaceutical Design; vol. 10, pp. 785-796 (2004).
Sigmund; "Viewpoint: Are Studies in Genetically Altered Mice Out of Control?"; Arterioscler Thromb Vasc Biol.; vol. 20, No. 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Sineshchekov et al.; "Intramolecular Proton Transfer in Channelrhodopsins"; Biophysical Journal; vol. 104, No. 4, pp. 807-817 (Feb. 2013).
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", NIPPON GANKA GAKKAI ZASSHI, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.," Light-Driven Chloride Ion Transport by Halorhodopsin from Natronobacterium pharaonic. 2. Chloride Release and Uptake, Protein Conformation Change, and Thermodynamics", Biochemistry (1995), 34(44):14500-14507.
Verma, et al.; "Gene therapy—promises, problems and prospects"; Nature; vol. 389, pp. 239-242 (Sep. 1997).
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.1-19.39.

(56) References Cited

OTHER PUBLICATIONS

Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Wang, et al.; "Simultaneous phase and size control of upconversion nanocrystals through lanthanide doping"; Nature; vol. 463, No. 7284, pp. 1061-1065 (Feb. 25, 2010).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Witten et. al., "Cholinergic Interneurons Control Local Circuit Activity and Cocaine Conditioning", Science, 2010, vol. 330, No. 6011: pp. 1677-1681.
Witten et. al., Supporting Online Material for: "Cholinergic Interneurons Control Local Circuit Activity and Cocaine Conditioning", Science, 2010, vol. 330: 17 pages.
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang "Multimodal fast optical interrogation of neural circuitry," Nature, 2007, vol. 446, pp. 633-641.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Definition of integral. Merriam-Webster Dictionary, retrieved on Mar. 20 2017; Retrieved from the internet: <http://www.merriam-webster.com/dictionary/integral>.
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).

(56) References Cited

OTHER PUBLICATIONS

Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Co-pending U.S. Appl. No. 14/886,763, filed Oct. 19, 2015.
Co-pending U.S. Appl. No. 14/911,405, filed Feb. 26, 2016.
Co-pending U.S. Appl. No. 15/008,214, filed Jan. 27, 2016.
Co-pending U.S. Appl. No. 15/059,159, filed Mar. 2, 2016.
Co-pending U.S. Appl. No. 15/095,519, filed Apr. 11, 2016.
Co-pending U.S. Appl. No. 15/097,925, filed Apr. 13, 2016.
Co-pending U.S. Appl. No. 15/147,772, filed May 5, 2016.
Co-pending U.S. Appl. No. 15/153,299, filed May 12, 2016.
Co-pending U.S. Appl. No. 15/153,305, filed May 12, 2016.
Co-pending U.S. Appl. No. 15/156,124, filed May 16, 2016.
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).

Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Masaki, et al.; "$\beta 2$-Adrenergic Receptor Regulation of the Cardiac L-Type Ca2+ Channel Coexpressed in a Fibroblast Cell Line"; Receptor; vol. 5, pp. 219-231 (1996).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Smith, et al.; "Proton binding sites involved in the activation of acid-sensing ion channel ASIC2a"; Neuroscience Letters; vol. 426, pp. 12-17 (2007).
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of *Limulus* Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Ahmad, et al. "Heterplogous expression of bovine rhodopsin in *Drosophila* photoreceptor cells" Invest Ophthalmol Vis Sci. 2006, 3722-3728.
Clare "Targeting Ion Channels for Drug Discovery" Discov Med. 2010 vol. 9 No. 46 pp. 1-6.
Clare "Functional Expression of Ion Channels in Mammalian Systems" Protein Science Encyclopedia A.R. Fersht (Ed.) 2008 pp. 79-109.
Reeves et al., "Structure and function in rhodosin: A tetracycline-inducible system in stable mammalian cell lines for high-level expression of opsin mutants" PNAS, 2002 vol. 99 No. 21 pp. 13413-13418.
Duvarci, et al "The bed Nucleus of the Stria Terminalis Mediates inter-individual variations in anxiety and fear", J. Neurosci., 29(33) 10357-10361 (2009).

(56) References Cited

OTHER PUBLICATIONS

Matsuda "Bed nucleus of stria terminalis (BNST)" Benshi Seishin Igaku (Molecular Psychiatric Medicine), 2009, vol. 9 No. 3, p. 46-49.
Neuropsychopharmacology, 2011, vol. 36 No. Suppl.1, p. S110 (Abstract No. 67).
Neuropsychopharmacology, 2012, vol. 38 No. Suppl.1, p. S48 (Abstract No. 37.2).
Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).

\* cited by examiner

SEQUENCE LISTING

```
<160> NUMBER OF SEQ ID NOS: 15

<210> SEQ ID NO 1
<211> LENGTH: 273
<212> TYPE: PRT
<213> ORGANISM: Natronomonas pharaonis

<400> SEQUENCE: 1

Val Thr Gln Arg Glu Leu Phe Glu Phe Val Leu Asn Asp Pro Leu Leu
 1               5                  10                  15

Ala Ser Ser Leu Tyr Ile Asn Ile Ala Leu Ala Gly Leu Ser Ile Leu
            20                  25                  30
```

```
Leu Phe Val Phe Met Thr Arg Gly Leu Asp Asp Pro Arg Ala Lys Leu
         35                  40                  45

Ile Ala Val Ser Thr Ile Leu Val Pro Val Val Ser Ile Ala Ser Tyr
 50                  55                  60

Thr Gly Leu Ala Ser Gly Leu Thr Ile Ser Val Leu Glu Met Pro Ala
 65                  70                  75                  80

Gly His Phe Ala Glu Gly Ser Ser Val Met Leu Gly Gly Glu Glu Val
                 85                  90                  95

Asp Gly Val Val Thr Met Trp Gly Arg Tyr Leu Thr Trp Ala Leu Ser
                100                 105                 110

Thr Pro Met Ile Leu Leu Ala Leu Gly Leu Leu Ala Gly Ser Asn Ala
                115                 120                 125

Thr Lys Leu Phe Thr Ala Ile Thr Phe Asp Ile Ala Met Cys Val Thr
                130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
                180                 185                 190

Phe Asn Thr Leu Lys Leu Leu Thr Val Val Met Trp Leu Gly Tyr Pro
                195                 200                 205

Ile Val Trp Ala Leu Gly Val Glu Gly Ile Ala Val Leu Pro Val Gly
                210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
                260                 265                 270

Asp

<210> SEQ ID NO 2
<211> LENGTH: 559
<212> TYPE: PRT
<213> ORGANISM: Artificial Sequence
<220> FEATURE:
<223> OTHER INFORMATION: Synthetic polypeptide

<400> SEQUENCE: 2

Met Thr Glu Thr Leu Pro Pro Val Thr Glu Ser Ala Val Ala Leu Gln
 1               5                  10                  15

Ala Glu Val Thr Gln Arg Glu Leu Phe Glu Phe Val Leu Asn Asp Pro
                20                  25                  30

Leu Leu Ala Ser Ser Leu Tyr Ile Asn Ile Ala Leu Ala Gly Leu Ser
                 35                  40                  45

Ile Leu Leu Phe Val Phe Met Thr Arg Gly Leu Asp Asp Pro Arg Ala
 50                  55                  60

Lys Leu Ile Ala Val Ser Thr Ile Leu Val Pro Val Val Ser Ile Ala
 65                  70                  75                  80

Ser Tyr Thr Gly Leu Ala Ser Gly Leu Thr Ile Ser Val Leu Glu Met
                 85                  90                  95

Pro Ala Gly His Phe Ala Glu Gly Ser Ser Val Met Leu Gly Gly Glu
                100                 105                 110

Glu Val Asp Gly Val Val Thr Met Trp Gly Arg Tyr Leu Thr Trp Ala
```

-continued

```
            115                 120                 125
Leu Ser Thr Pro Met Ile Leu Ala Leu Gly Leu Ala Gly Ser
        130                 135                 140

Asn Ala Thr Lys Leu Phe Thr Ala Ile Thr Phe Asp Ile Ala Met Cys
145                 150                 155                 160

Val Thr Gly Leu Ala Ala Leu Thr Thr Ser Ser His Leu Met Arg
                165                 170                 175

Trp Phe Trp Tyr Ala Ile Ser Cys Ala Cys Phe Leu Val Val Leu Tyr
                180                 185                 190

Ile Leu Leu Val Glu Trp Ala Gln Asp Ala Lys Ala Ala Gly Thr Ala
                195                 200                 205

Asp Met Phe Asn Thr Leu Lys Leu Leu Thr Val Val Met Trp Leu Gly
        210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
                260                 265                 270

Val Val Ser Gly Ser Ile Leu Asp Val Pro Ser Ala Ser Gly Thr Pro
        275                 280                 285

Ala Asp Asp Ala Ala Lys Ser Arg Ile Thr Ser Glu Gly Glu Tyr
        290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
                325                 330                 335

Asn Gly His Lys Phe Ser Val Ser Gly Glu Gly Glu Gly Asp Ala Thr
                340                 345                 350

Tyr Gly Lys Leu Thr Leu Lys Phe Ile Cys Thr Thr Gly Lys Leu Pro
                355                 360                 365

Val Pro Trp Pro Thr Leu Val Thr Thr Phe Gly Tyr Gly Leu Gln Cys
        370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
                405                 410                 415

Asp Gly Asn Tyr Lys Thr Arg Ala Glu Val Lys Phe Glu Gly Asp Thr
                420                 425                 430

Leu Val Asn Arg Ile Glu Leu Lys Gly Ile Asp Phe Lys Glu Asp Gly
                435                 440                 445

Asn Ile Leu Gly His Lys Leu Glu Tyr Asn Tyr Asn Ser His Asn Val
        450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
                485                 490                 495

Gln Gln Asn Thr Pro Ile Gly Asp Gly Pro Val Leu Leu Pro Asp Asn
                500                 505                 510

His Tyr Leu Ser Tyr Gln Ser Ala Leu Ser Lys Asp Pro Asn Glu Lys
                515                 520                 525

Arg Asp His Met Val Leu Leu Glu Phe Val Thr Ala Ala Gly Ile Thr
        530                 535                 540
```

Leu Gly Met Asp Glu Leu Tyr Lys Phe Cys Tyr Glu Asn Glu Val
545                 550                 555

<210> SEQ ID NO 3
<211> LENGTH: 542
<212> TYPE: PRT
<213> ORGANISM: Artificial Sequence
<220> FEATURE:
<223> OTHER INFORMATION: Synthetic polypeptide

<400> SEQUENCE: 3

Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
                20                  25                  30

Leu Leu Phe Val Phe Met Thr Arg Gly Leu Asp Asp Pro Arg Ala Lys
            35                  40                  45

Leu Ile Ala Val Ser Thr Ile Leu Val Pro Val Ser Ile Ala Ser
        50                  55                  60

Tyr Thr Gly Leu Ala Ser Gly Leu Thr Ile Ser Val Leu Glu Met Pro
65                  70                  75                  80

Ala Gly His Phe Ala Glu Gly Ser Ser Val Met Leu Gly Gly Glu Glu
                85                  90                  95

Val Asp Gly Val Val Thr Met Trp Gly Arg Tyr Leu Thr Trp Ala Leu
            100                 105                 110

Ser Thr Pro Met Ile Leu Leu Ala Leu Gly Leu Leu Ala Gly Ser Asn
        115                 120                 125

Ala Thr Lys Leu Phe Thr Ala Ile Thr Phe Asp Ile Ala Met Cys Val
130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Leu Thr Val Val Met Trp Leu Gly Tyr
        195                 200                 205

Pro Ile Val Trp Ala Leu Gly Val Glu Gly Ile Ala Val Leu Pro Val
210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
            260                 265                 270

Asp Asp Ala Ala Ala Lys Ser Arg Ile Thr Ser Glu Gly Glu Tyr Ile
        275                 280                 285

Pro Leu Asp Gln Ile Asp Ile Asn Val Val Ser Lys Gly Glu Glu Leu
290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Glu Gly Asp Ala Thr Tyr
                325                 330                 335

Gly Lys Leu Thr Leu Lys Phe Ile Cys Thr Thr Gly Lys Leu Pro Val
            340                 345                 350

```
Pro Trp Pro Thr Leu Val Thr Thr Phe Gly Tyr Gly Leu Gln Cys Phe
        355                 360                 365

Ala Arg Tyr Pro Asp His Met Lys Gln His Asp Phe Phe Lys Ser Ala
        370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
                405                 410                 415

Val Asn Arg Ile Glu Leu Lys Gly Ile Asp Phe Lys Glu Asp Gly Asn
                420                 425                 430

Ile Leu Gly His Lys Leu Glu Tyr Asn Tyr Asn Ser His Asn Val Tyr
                435                 440                 445

Ile Met Ala Asp Lys Gln Lys Asn Gly Ile Lys Val Asn Phe Lys Ile
                450                 455                 460

Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
                485                 490                 495

Tyr Leu Ser Tyr Gln Ser Ala Leu Ser Lys Asp Pro Asn Glu Lys Arg
                500                 505                 510

Asp His Met Val Leu Leu Glu Phe Val Thr Ala Ala Gly Ile Thr Leu
                515                 520                 525

Gly Met Asp Glu Leu Tyr Lys Phe Cys Tyr Glu Asn Glu Val
                530                 535                 540

<210> SEQ ID NO 4
<211> LENGTH: 223
<212> TYPE: PRT
<213> ORGANISM: Guillardia theta

<400> SEQUENCE: 4

Ala Ser Ser Phe Gly Lys Ala Leu Leu Glu Phe Val Phe Ile Val Phe
1               5                   10                  15

Ala Cys Ile Thr Leu Leu Leu Gly Ile Asn Ala Ala Lys Ser Lys Ala
                20                  25                  30

Ala Ser Arg Val Leu Phe Pro Ala Thr Phe Val Thr Gly Ile Ala Ser
        35                  40                  45

Ile Ala Tyr Phe Ser Met Ala Ser Gly Gly Gly Trp Val Ile Ala Pro
50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
                85                  90                  95

Trp Asp Ile Met Ala Leu Cys Leu Ser Asp Val Leu Met Ile Ala Thr
            100                 105                 110

Gly Ala Phe Gly Ser Leu Thr Val Gly Asn Val Lys Trp Val Trp Trp
        115                 120                 125

Phe Phe Gly Met Cys Trp Phe Leu His Ile Ile Phe Ala Leu Gly Lys
130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
```

```
              180                 185                 190
Glu Val Leu Ile Tyr Gly Val Leu Asp Val Ile Ser Lys Ala Val Phe
            195                 200                 205
Gly Leu Ile Leu Met Ser Gly Ala Ala Thr Gly Tyr Glu Ser Ile
        210                 215                 220

<210> SEQ ID NO 5
<211> LENGTH: 310
<212> TYPE: PRT
<213> ORGANISM: Chlamydomonas reinhardtii

<400> SEQUENCE: 5

Met Asp Tyr Gly Gly Ala Leu Ser Ala Val Gly Arg Glu Leu Leu Phe
1               5                   10                  15
Val Thr Asn Pro Val Val Asn Gly Ser Val Leu Val Pro Glu Asp
            20                  25                  30
Gln Cys Tyr Cys Ala Gly Trp Ile Glu Ser Arg Gly Thr Asn Gly Ala
            35                  40                  45
Gln Thr Ala Ser Asn Val Leu Gln Trp Leu Ala Ala Gly Phe Ser Ile
        50                  55                  60
Leu Leu Leu Met Phe Tyr Ala Tyr Gln Thr Trp Lys Ser Thr Cys Gly
65                  70                  75                  80
Trp Glu Glu Ile Tyr Val Cys Ala Ile Glu Met Val Lys Val Ile Leu
                85                  90                  95
Glu Phe Phe Phe Glu Phe Lys Asn Pro Ser Met Leu Tyr Leu Ala Thr
            100                 105                 110
Gly His Arg Val Gln Trp Leu Arg Tyr Ala Glu Trp Leu Leu Thr Cys
        115                 120                 125
Pro Val Ile Leu Ile His Leu Ser Asn Leu Thr Gly Leu Ser Asn Asp
130                 135                 140
Tyr Ser Arg Arg Thr Met Gly Leu Leu Val Ser Asp Ile Gly Thr Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
        195                 200                 205
Arg Gln Val Val Thr Gly Met Ala Trp Leu Phe Phe Val Ser Trp Gly
210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
        275                 280                 285
Ile Gly Gly Thr Glu Ile Glu Val Glu Thr Leu Val Glu Asp Glu Ala
290                 295                 300
Glu Ala Gly Ala Val Pro
305             310

<210> SEQ ID NO 6
<211> LENGTH: 310
```

```
<212> TYPE: PRT
<213> ORGANISM: Artificial Sequence
<220> FEATURE:
<223> OTHER INFORMATION: Synthetic polypeptide

<400> SEQUENCE: 6

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 7
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 7

Met Asp Tyr Gly Gly Ala Leu Ser Ala Val Gly Arg Glu Leu Leu Phe
1               5                   10                  15
```

```
Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 8
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60
```

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
            130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
            165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Glu Asp
            340

<210> SEQ ID NO 9
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 9

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
            50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 10
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 10

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 11
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 11

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

```
Thr Trp Lys Ser Thr Cys Gly Trp Glu Thr Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 12
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

Lys Ser Arg Ile Thr Ser Glu Gly Glu Tyr Ile Pro Leu Asp Gln Ile
1               5                   10                  15

Asp Ile Asn Val
            20

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(2)
<223> OTHER INFORMATION: x = any amino acid

<400> SEQUENCE: 13

Phe Xaa Tyr Glu Asn Glu
1               5
```

```
<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Phe Cys Tyr Glu Asn Glu Val
 1               5

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide

<400> SEQUENCE: 15

Met Thr Glu Thr Leu Pro Pro Val Thr Glu Ser Ala Val Ala Leu Gln
 1               5                  10                  15

Ala Glu
```

UPCONVERSION OF LIGHT FOR USE IN OPTOGENETIC METHODS

CROSS REFERENCE TO RELATED APPLICATION

This application is a continuation of U.S. patent application Ser. No. 13/882,703 filed Apr. 30, 2013, which is a national stage filing under 35 U.S.C. § 371 of PCT/US2011/059287, filed Nov. 4, 2011, which claims priority to U.S. Provisional Application No. 61/410,729, filed Nov. 5, 2010, each of which applications is incorporated herein by reference in its entirety.

FIELD OF THE INVENTION

This application pertains to compositions comprising lanthanide-doped nanoparticles which upconvert electromagnetic radiation from infrared or near infrared wavelengths into the visible light spectrum and methods of using lanthanide-doped nanoparticles to deliver light to activate light-responsive opsin proteins expressed in neurons and selectively alter the membrane polarization state of the neurons.

BACKGROUND

Optogenetics is the combination of genetic and optical methods used to control specific events in targeted cells of living tissue, even within freely moving mammals and other animals, with the temporal precision (millisecond-timescale) needed to keep pace with functioning intact biological systems. The hallmark of optogenetics is the introduction of fast light-responsive opsin channel or pump proteins to the plasma membranes of target neuronal cells that allow temporally precise manipulation of neuronal membrane potential while maintaining cell-type resolution through the use of specific targeting mechanisms. Among the microbial opsins which can be used to investigate the function of neural systems are the halorhodopsins (NpHRs), used to promote membrane hyperpolarization when illuminated, and the channelrhodopsins, used to depolarize membranes upon exposure to light. In just a few short years, the field of optogenetics has furthered the fundamental scientific understanding of how specific cell types contribute to the function of biological tissues, such as neural circuits, in vivo. Moreover, on the clinical side, optogenetics-driven research has led to insights into the neurological mechanisms underlying complex mammalian behaviors such as anxiety, memory, fear, and addiction.

In spite of these advances, use of optogenetic methods in animals suffers from the significant drawback of requiring the animal to either be tethered to a light source or to have a light source surgically implanted into the animal. Moreover, when optogenetic methods are used to alter the function of neurons in the brain, a light source must be placed in proximity to those neurons. This requires drilling a hole in the animal's skull and also presents practical difficulties when the brain region of interest is located deep within the brain itself. Since light poorly passes through neural tissue, this necessitates inserting a fiber optic light source into the brain, which can result in unintended damage to surrounding brain tissue.

What is needed, therefore, is a method to non-invasively deliver light to neurons located within the brain and the peripheral nervous system of animals expressing light-responsive opsin proteins on the plasma membranes of neural cells.

Throughout this specification, references are made to publications (e.g., scientific articles), patent applications, patents, etc., all of which are herein incorporated by reference in their entirety.

SUMMARY OF THE INVENTION

Provided herein are compositions and methods for non-invasively delivering light to neurons expressing light-responsive opsin proteins on neural plasma membranes via the use of nanoparticles capable of upshifting electromagnetic radiation from wavelengths associated with the infrared (IR) or near infrared (NIR) spectrum into wavelengths associated with visible light.

Accordingly, provided herein is a method to depolarize the plasma membrane of a neural cell in an individual comprising: (a) placing a plurality of lanthanide-doped nanoparticles in proximity to the neural cell; and (b) exposing the plurality of nanoparticles to electromagnetic radiation in the infrared (IR) or near infrared (NIR) spectrum, wherein the electromagnetic radiation in the IR or NIR spectrum is upconverted into light in the visible spectrum by the nanoparticles, and wherein a light-responsive opsin is expressed on the plasma membrane of the neural cells and activation of the opsin by the light in the visible spectrum induces the depolarization of the plasma membrane.

In other aspects, provided herein is a method to depolarize the plasma membrane of a neural cell in an individual comprising: (a) administering a polynucleotide encoding a light-responsive opsin to an individual, wherein the light-responsive protein is expressed on the plasma membrane of a neural cell in the individual, and the opsin is capable of inducing membrane depolarization of the neural cell when illuminated with light; (b) administering a plurality of lanthanide-doped nanoparticles in proximity to the neural cell; and (c) exposing the plurality of nanoparticles to electromagnetic radiation in the infrared (IR) or near infrared (NIR) spectrum, wherein the electromagnetic radiation in the IR or NIR spectrum is upconverted into light in the visible spectrum and the activation of the opsin by the light in the visible spectrum induces the depolarization of the plasma membrane.

In some aspects, provided herein is a method to hyperpolarize the plasma membrane of a neural cell in an individual comprising: (a) placing a plurality of lanthanide-doped nanoparticles in proximity to the neural cell; and (b) exposing the plurality of nanoparticles to electromagnetic radiation in the infrared (IR) or near infrared (NIR) spectrum, wherein the electromagnetic radiation in the IR or NIR spectrum is upconverted into light in the visible spectrum by the nanoparticles, and wherein a light-responsive opsin is expressed on the plasma membrane and activation of the opsin by the light in the visible spectrum induces the hyperpolarization of the plasma membrane.

In yet other aspects, provided herein is a method to hyperpolarize the plasma membrane of a neural cell in an individual comprising: (a) administering a polynucleotide encoding a light-responsive opsin to an individual, wherein the light-responsive protein is expressed on the plasma membrane of a neural cell in the individual, and the opsin is capable of inducing membrane hyperpolarization of the neural cell when illuminated with light; (b) administering a plurality of lanthanide-doped nanoparticles in proximity to the neural cell; and (c) exposing the plurality of nanoparticles to electromagnetic radiation in the infrared (IR) or near infrared (NIR) spectrum, wherein the electromagnetic radiation in the IR or NIR spectrum is upconverted into light in the visible spectrum and the activation of the opsin by the light in the visible spectrum induces the hyperpolarization of the plasma membrane.

The present disclosure is directed to apparatuses and methods involving upconversion for deep delivery of light in vivo. Aspects of the present disclosure relate generally to delivery of light to tissue in vivo using upconversion of near infrared light to the visible light spectrum and methods relating to the applications discussed herein.

Certain aspects of the present disclosure are directed to a light source that is implanted within living tissue. Nanoparticles from the nanoparticle solution anchor to a target cell population that includes cells expressing light responsive channels/opsins. The nanoparticles are configured to respond to receipt of light of a first wavelength by emitting light of a second, different wavelength. For example, the nanoparticles can upconvert received light and thereby emit light of a higher frequency.

Embodiments of the present disclosure are directed towards injection of a site of interest with a virus, caring an opsin gene and a nanoparticle solution. The virus causes a target cell population at the site of interest to express the opsin gene. Various different light sources are possible. The use of different wavelengths can be particularly useful for facilitating the use of different (external) light sources, e.g., as certain wavelengths exhibit corresponding decreases in absorption by tissue of the brain or otherwise.

Consistent with a particular embodiment of the present disclosure, a light-emitting diode ("LED") is placed on a portion of a skull that has been thinned. The LED is placed under the skin near the thinned portion of the skull, and the location and/or orientation of the LED is chosen, at least in part, based on the location of the target cell population. For example, the LED can be placed to reduce the distance between the LED and the target cell population and oriented accordingly.

In certain more specific aspects of the present disclosure, light from the LED travels through surrounding tissue to the nanoparticles. When (near) infrared light hits the nanoparticles, the nanoparticles absorb the infrared (IR) photons and emit visible photons. The visible photons are then absorbed by the opsins expressed within the target cell population causing a response therein (e.g., triggering neural excitation or inhibition).

The LED can be powered by a battery similar to those used for pacemakers. The LED can emit light in the infrared spectrum, and particularly between 700 nm-1000 nm, which can travel through the skull and intervening tissue. The light emitted from the nanoparticles has a spectra centered between 450-550 nm. The wavelength of the light emitted is dependent on characteristics of the nanoparticle.

The above overview is not intended to describe each illustrated embodiment or every implementation of the present disclosure.

BRIEF DESCRIPTION OF THE DRAWINGS

Various example embodiments may be more completely understood in consideration of the following description and the accompanying drawings, in which.

Figures 1, 2:
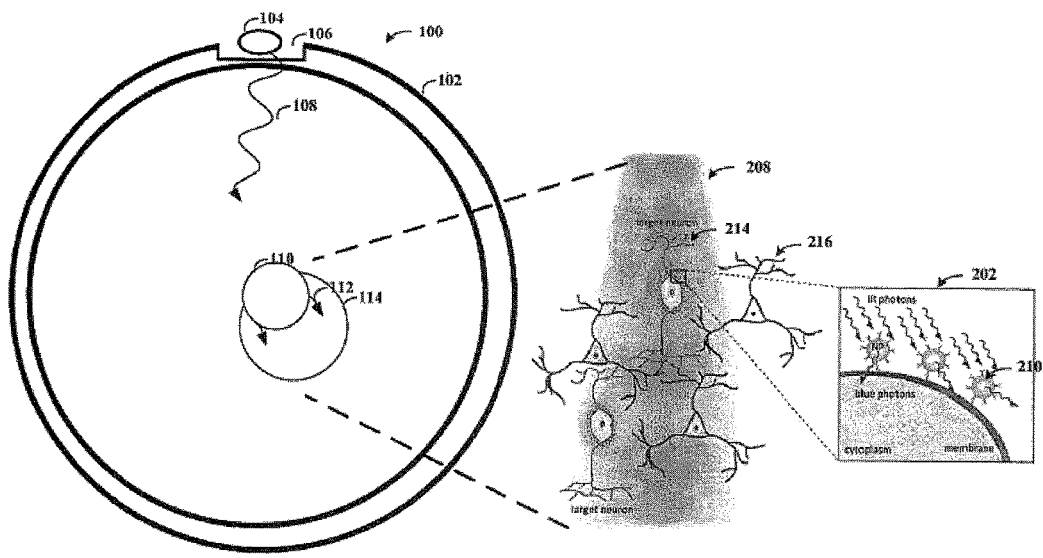
FIG. 1 shows a cross section of a skull, consistent with an embodiment of the present disclosure.
FIG. 2 shows light delivery to target neurons, consistent with an embodiment of the present disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the scope of the present disclosure including aspects defined in the claims.

DETAILED DESCRIPTION

This invention provides, inter alia, compositions and methods for delivering light to neural cells expressing one or more light-responsive opsin proteins on the plasma membranes of those neural cells. The inventors have discovered that nanoparticles doped with a lanthanide metal (for example, Gadolinium) that converts infrared (IR) or near infrared (NIR) electromagnetic radiation into wavelengths corresponding to the visible light spectrum can be used to activate light-responsive opsin proteins on the plasma membrane of a neural cell and selectively alter the membrane polarization state of the cell. Unlike visible light, IR or NIR electromagnetic energy readily penetrates biological tissues. For example, NIR can penetrate biological tissues for distances of up to 4 centimeters (Heyward & Dale Wagner, "*Applied Body Composition Assessment*", 2nd edition (2004), p. 100). Certain equations useful for calculating light penetration in tissue as a function of wavelength are disclosed in U.S. Pat. No. 7,043,287, the contents of which are incorporated herein by reference. Similarly, U.S. Patent Application Publication No. 2007/0027411 discloses that near infrared Low Level Laser Treatment light penetrates the body to a depth of between 3-5 cm. Therefore, use of IR or NIR sources of electromagnetic radiation in optogenetic methods can alleviate the need to place a light source in direct proximity to neural cells. In particular, for optogenetic techniques in the brain, use of lanthanide-doped nanoparticles in combination with IR or NIR electromagnetic energy can permit activation of the opsin protein without the need to puncture the skull or insert a fiber optic light source into the brain. Similarly, in the peripheral nervous system, opsin-expressing nerves can be activated via IR or NIR sources placed under the skin or worn against the skin.

General Techniques

The practice of the present invention will employ, unless otherwise indicated, conventional techniques of molecular biology, microbiology, cell biology, biochemistry, nucleic acid chemistry, immunology, and physiology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999), *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000), *Handbook of Experimental Immunology*, 4th edition (D. M. Weir & C. C. Blackwell, eds., Blackwell Science Inc., 1987), and *Gene Transfer*

*Vectors for Mammalian Cells* (J. M. Miller & M. P. Calos, eds., 1987). Other useful references include Harrison's *Principles of Internal Medicine* (McGraw Hill; J. Isseleacher et al., eds.) and *Lanthanide Luminescence: Photophysical, Analytical and Biological Aspects* (Springer-Verlag, Berlin, Heidelberg; Hanninen & Harma, eds., 2011).

Definitions

As used herein, "infrared" or "near infrared" or "infrared light" or "near infrared light" refers to electromagnetic radiation in the spectrum immediately above that of visible light, measured from the nominal edge of visible red light at 0.74 µm, and extending to 300 µm. These wavelengths correspond to a frequency range of approximately 1 to 400 THz. In particular, "near infrared" or "near infrared light" also refers to electromagnetic radiation measuring 0.75-1.4 µm in wavelength, defined by the water absorption.

"Visible light" is defined as electromagnetic radiation with wavelengths between 380 nm and 750 nm. In general, "electromagnetic radiation," including light, is generated by the acceleration and deceleration or changes in movement (vibration) of electrically charged particles, such as parts of molecules (or adjacent atoms) with high thermal energy, or electrons in atoms (or molecules).

The term "nanoparticles" as used herein, can also refer to nanocrystals, nanorods, nanoclusters, clusters, particles, dots, quantum dots, small particles, and nanostructured materials. The term "nanoparticle" encompasses all materials with small size (generally, though not necessarily) less than 100 nm associated with quantum size effects.

An "individual" is a mammal including a human. Mammals include, but are not limited to, farm animals, sport animals, pets, primates, mice and rats. Individuals also include companion animals including, but not limited to, dogs and cats. In some aspects, an individual is a non-human animal, such as a mammal. In another aspect, an individual is a human.

As used herein, the singular form "a", "an", and "the" includes plural references unless indicated otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Lanthanide-Doped Nanoparticles

In materials science, doping is commonly used to incorporate specific species of ions or atoms into a host lattice core structure to produce hybrid materials with new and useful properties. When synthesizing nanoparticles, doping can influence not only the size and shape of the particles, but also other properties, such as the ability to convert near infrared (NIR) excitation into a visible emission of light.

The lanthanide metals, or lanthanoids (also known as the "Rare Earth" metals), are elements of atomic number 57 (Lanthanum) through 71 (Lutetium), and often include Yttrium (atomic number 39) and Scandium (atomic number 21) because of their chemical similarities. Lanthanide ions exhibit unique luminescent properties, including the ability to convert near infrared long-wavelength excitation radiation into shorter visible wavelengths through a process known as photon upconversion. Lanthanides usually exist as trivalent cations, in which case their electronic configuration is (Xe) 4f, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. Additionally, the f-f electronic transitions of lanthanides are LaPorte forbidden, leading to long excited state lifetimes, in the micro- to millisecond range.

In some embodiments, any known method can be used to synthesize lanthanide-doped nanoparticles. Such methods are well known in the art (See, e.g., Xu & Li, 2007, *Clin Chem.*, 53(8):1503-10; Wang et al., 2010, *Nature*, 463 (7284):1061-5; U.S. Patent Application Publication Nos.: 2003/0030067 and 2010/0261263; and U.S. Pat. No. 7,550,201, the disclosures of each of which are incorporated herein by reference in their entireties). For example, in some embodiments, lanthanide-doped nanorods can be synthesized with a $NaYF_4$ dielectric core, wherein a DI water solution (1.5 ml) of 0.3 g NaOH is mixed with 5 ml of ethanol and 5 ml of oleic acid under stirring. To the resulting mixture is selectively added 2 ml of $RECl_3$ (0.2 M, RE=Y, Yb, Er, Gd, Sm, Nd or La) and 1 ml of $NH_4F$ (2 M). The solution is then transferred into an autoclave and heated at 200° C. for 2 h. Nanorods are then obtained by centrifugation, washed with water and ethanol several times, and finally re-dispersed in cyclohexane. In another non-limiting example, nanoparticles can be synthesized using 2 ml of $RECl_3$ (0.2 M, RE=Y, Yb, Er, Gd, or Tm) in methanol added to a flask containing 3 ml oleic acid and 7 ml of 1-octadecene. This solution is then heated to 160° C. for 30 min and cooled down to room temperature. Thereafter, a 5 ml methanol solution of $NH_4F$ (1.6 mmol) and NaOH (1 mmol) is added and the solution is stirred for 30 min. After methanol evaporation, the solution is next heated to 300° C. under argon for 1.5 h and cooled down to room temperature. The resulting nanoparticles are precipitated by the addition of ethanol, collected by centrifugation, washed with methanol and ethanol several times, and finally re-dispersed in cyclohexane.

In one embodiment, the materials for the lanthanide-doped nanoparticle core can include a wide variety of dielectric materials. In various embodiments, the dielectric core can include lanthanide-doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence, suitable dielectric core materials include, but are not limited to, $Y_2O_3$, $Y_2O_2S$, $NaYF_4$, $NaYbF4$, Na doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. In one embodiment, the dielectric nanoparticle core is $NaYF_4$. These dielectric cores can be doped with one or more Er, Eu, Yb, Tm, Nd, Tb, Ce, Y, U, Pr, La, Gd and other rare-earth species or a combination thereof. In one embodiment, the dielectric core material is doped with Gd. In another embodiment, the lanthanide-doped nanoparticle comprises $NaYF_4$:Yb/X/Gd, wherein X is Er, Tm, or Er/Tm. In some embodiments, the lanthanide-doped nanoparticles comprise a $NaYF_4$:Yb/Er (18/2 mol %) dielectric core doped with any of about 0 mol %, about 5 mol %, about 10 mol %, about 15 mol %, about 20 mol %, about 25 mol %, about 30 mol %, about 35 mol %, about 40 mol %, about 45 mol %, about 50 mol %, about 55 mol %, about or 60 mol % $Gd^{3+}$ ions, inclusive, including any mol % in between these values. In other embodiments, the lanthanide-doped nanoparticles comprise a $NaYF_4$:Yb/Er (18/2 mol %) dielectric core doped with any of about 0 mol %, about 5 mol %, about 10 mol %, about 15 mol %, about 20 mol %, about 25 mol %, or about 30 mol % $Yb^{3+}$ ions, inclusive, including any mol % in between these values. In yet other embodiments, the lanthanide-doped nanoparticles comprise a $NaYF_4$:Yb/Er (18/2 mol %) dielectric core doped with any of about 0 mol %, about 5 mol %, about 10 mol %, about 15 mol %, about 20 mol %, about 25 mol %, or about 30 mol % $Er^{3+}$ ions, inclusive, including any mol % in between these values. In other embodiments, the lanthanide-doped nanoparticles comprise a $NaYF_4$:Yb/Er (18/2 mol %) dielectric core doped with any of about 0 mol %, about 5 mol %, about 10 mol %, about 15 mol %, about 20 mol %, about 25 mol %, or about 30 mol % $Tm^{3+}$ ions, inclusive, including any mol % in between these values. In another embodiment, the lanthanide-doped nanoparticle is selected from the group consisting of $NaYF_4$:Yb/Er/Gd (18/2/5 mol %), $NaYF_4$:Yb/Tm/Er/Gd (20/0.2/0.1/5 mol %), $NaYF_4$:Yb/Tm/Er/Gd (20/0.2/0.05/5 mol %), and $NaYF_4$:Yb/Tm/Gd (20/0.2/5 mol %).

In some aspects, the lanthanide-doped nanoparticles disclosed herein are conjugated to one or more delivery molecules to target them to one or more molecules expressed on the surface of a neural cell of interest (such as a neural cell expressing one or more light-responsive opsin proteins on its plasma membrane). These can include, without limitation, antibodies or fragments thereof, small molecules, as well as lectins or any other carbohydrate motif. The delivery molecules ensure that the lanthanide-doped nanoparticles remain in close proximity to the opsin proteins to permit activation upon upconversion of IR or NIR electromagnetic radiation. Antibody conjugation to nanoparticles is well-known in the art (See, e.g., U.S. Patent Application Publication No.: 2010/0209352 and 2008/0267876, the contents of each of which are incorporated by reference herein in their entireties).

In another aspect, lanthanide-doped nanoparticles can be embedded or trapped within a biocompatible material which is surgically placed proximal to (such as adjacent to or around) the neural cell of interest (such as a neural cell expressing one or more light-responsive opsin proteins on its plasma membrane). In some embodiments, the biocompatible material is transparent, so that visible light produced by the upconversion of IR or NIR electromagnetic radiation by the lanthanide-doped nanoparticles can reach the light-responsive opsin proteins expressed on the surface of the neural cell of interest. The biocompatible materials used to embed or trap the lanthanide-doped nanoparticles can include, but are not limited to, Ioplex materials and other hydrogels such as those based on 2-hydroxyethyl methacrylate or acrylamide, and poly ether polyurethane ureas (PEUU) including Biomer (Ethicon Corp.), Avcothane (Avco-Everrett Laboratories), polyethylene, polypropylene, polytetrafluoroethylene (Gore-Tex), poly(vinylchloride), polydimethylsiloxane, an ethylene-acrylic acid copolymer, knitted or woven Dacron, polyester-polyurethane, polyurethane, polycarbonatepolyurethane (Corethane), polyamide (Nylon) and polystyrene. In one embodiment, the biocompatible material can be polydimethylsiloxane (PDMS). Additional compounds that may be used for embedding and/or trapping the lanthanide-doped nanoparticles disclosed herein are described in Kirk-Othmer, *Encyclopedia of Chemical Technology*, 3rd Edition 1982 (Vol. 19, pp. 275-313, and Vol. 18, pp. 219-2220), van der Giessen et al., 1996, *Circulation*, 94:1690-1997 (1996), U.S. Patent Application Publication No.: 2011/0054305, and U.S. Pat. No. 6,491,965, the contents of each which are incorporated herein by reference in their entireties.

Light-Responsive Opsin Proteins

Provided herein are optogenetic-based compositions for selectively hyperpolarizing or depolarizing neurons of the central or peripheral nervous system. Optogenetics refers to the combination of genetic and optical methods used to control specific events in targeted cells of living tissue, even within freely moving mammals and other animals, with the temporal precision (millisecond-timescale) needed to keep pace with functioning intact biological systems. Optogenetics requires the introduction of fast light-responsive channel or pump proteins to the plasma membranes of target neuronal cells that allow temporally precise manipulation of neuronal membrane potential while maintaining cell-type resolution through the use of specific targeting mechanisms.

Light-responsive opsins that may be used in the present invention include opsins that induce hyperpolarization in neurons by light and opsins that induce depolarization in neurons by light. Examples of opsins are shown in Tables 1 and 2 below.

Table 1 shows identified opsins for inhibition of cellular acitivty across the visible spectrum:

| Opsin Type | Biological Origin | Wavelength Sensitivity | Defined action |
|---|---|---|---|
| NpHR | *Natronomonas pharaonis* | 589 nm max | Inhibition (hyperpolarization) |
| BR | *Halobacterium helobium* | 570 nm max | Inhibition (hyperpolarization) |
| AR | *Acetabulaira acetabulum* | 518 nm max | Inhibition (hyperpolarization) |
| GtR3 | *Guillardia theta* | 472 nm max | Inhibition (hyperpolarization) |
| Mac | *Leptosphaeria maculans* | 470-500 nm max | Inhibition (hyperpolarization) |
| NpHr3.0 | *Natronomonas pharaonis* | 680 nm utility 589 nm max | Inhibition (hyperpolarization) |
| NpHR3.1 | *Natronomonas pharaonis* | 680 nm utility 589 nm max | Inhibition (hyperpolarization) |

Table 2 show identified opsins for excitation and modulation across the visible specturm:

| Opsin Type | Biological Origin | Wavelength Sensitivity | Defined action |
|---|---|---|---|
| VChR1 | *Volvox carteri* | 589 nm utility 535 nm max | Excitation (depolarization) |
| DChR | *Dunaliella salina* | 500 nm max | Excitation (depolarization) |
| ChR2 | *Chlamydomonas reinhardtii* | 470 nm max 380-405 nm utility | Excitation (depolarization) |
| ChETA | *Chlamydomonas reinhardtii* | 470 nm max 380-405 nm utility | Excitation (depolarization) |
| SFO | *Chlamydomonas reinhardtii* | 470 nm max 530 nm max | Excitation (depolarization) Inactivation |
| SSFO | *Chlamydomonas reinhardtii* | 445 nm max 590 nm; 390-400 nm | Step-like activation (depolarization) Inactivation |
| C1V1 | *Volvox carteri* and *Chlamydomonas reinhardtii* | 542 nm max | Excitation (depolarization) |
| C1V1 E122 | *Volvox carteri* and *Chlamydomonas reinhardtii* | 546 nm max | Excitation (depolarization) |

| Opsin Type | Biological Origin | Wavelength Sensitivity | Defined action |
|---|---|---|---|
| C1V1 E162 | Volvox carteri and Chlamydomonas reinhardtii | 542 nm max | Excitation (depolarization) |
| C1V1 E122/E162 | Volvox carteri and Chlamydomonas reinhardtii | 546 nm max | Excitation (depolarization) |

As used herein, a light-responsive opsin (such as NpHR, BR, AR, GtR3, Mac, ChR2, VChR1, DChR, and ChETA) includes naturally occurring protein and functional variants, fragments, fusion proteins comprising the fragments, or the full length protein. For example, the signal peptide may be deleted. A variant may have an amino acid sequence at least about any of 90%, 91%, 92%, 93%, 94%, 95%, 96%, 97%, 98%, 99%, or 100% identical to the naturally occurring protein sequence. A functional variant may have the same or similar hyperpolarization function or depolarization function as the naturally occurring protein.

Enhanced Intracellular Transport Amino Acid Motifs

The present disclosure provides for the modification of light-responsive opsin proteins expressed in a cell by the addition of one or more amino acid sequence motifs which enhance transport to the plasma membranes of mammalian cells. Light-responsive opsin proteins having components derived from evolutionarily simpler organisms may not be expressed or tolerated by mammalian cells or may exhibit impaired subcellular localization when expressed at high levels in mammalian cells. Consequently, in some embodiments, the light-responsive opsin proteins expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive opsin protein transport to the plasma membranes of mammalian cells can be fused to the N-terminus, the C-terminus, or to both the N- and C-terminal ends of the light-responsive opsin protein. Optionally, the light-responsive opsin protein and the one or more amino acid sequence motifs may be separated by a linker. In some embodiments, the light-responsive opsin protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV.

Additional protein motifs which can enhance light-responsive opsin protein transport to the plasma membrane of a cell are described in U.S. Patent Application Publication No. 2009/0093403, which is incorporated herein by reference in its entirety. In some embodiments, the signal peptide sequence in the protein can be deleted or substituted with a signal peptide sequence from a different protein.

Light-Responsive Chloride Pumps

In some aspects, the light-responsive opsin proteins described herein are light-responsive chloride pumps. In some aspects of the methods provided herein, one or more members of the Halorhodopsin family of light-responsive chloride pumps are expressed on the plasma membranes of neurons of the central and peripheral nervous systems.

In some aspects, said one or more light-responsive chloride pump proteins expressed on the plasma membranes of nerve cells of the central or peripheral nervous systems can be derived from *Natronomonas pharaonis*. In some embodiments, the light-responsive chloride pump proteins can be responsive to amber light as well as red light and can mediate a hyperpolarizing current in the interneuron when the light-responsive chloride pump proteins are illuminated with amber or red light. The wavelength of light which can activate the light-responsive chloride pumps can be between about 580 and about 630 nm. In some embodiments, the light can be at a wavelength of about 590 nm or the light can have a wavelength greater than about 630 nm (e.g. less than about 740 nm). In another embodiment, the light has a wavelength of around 630 nm. In some embodiments, the light-responsive chloride pump protein can hyperpolarize a neural membrane for at least about 90 minutes when exposed to a continuous pulse of light. In some embodiments, the light-responsive chloride pump protein can comprise an amino acid sequence at least about 90%, 91%, 92%, 93%, 94%, 95%, 96%, 97%, 98%, 99%, or 100% identical to the sequence shown in SEQ ID NO: 1. Additionally, the light-responsive chloride pump protein can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive chloride pump protein contains one or more conservative amino acid substitutions. In some embodiments, the light-responsive protein contains one or more non-conservative amino acid substitutions. The light-responsive protein comprising substitutions, deletions, and/or insertions introduced into the native amino acid sequence suitably retains the ability to hyperpolarize the plasma membrane of a neuronal cell in response to light.

Additionally, in other aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 1 and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal can comprise the amino acid sequence FXYENE, where X can be any amino acid. In another embodiment, the ER export signal can comprise the amino acid sequence VXXSL, where X can be any amino acid. In some embodiments, the ER export signal can comprise the amino acid sequence FCYENEV.

In other aspects, the light-responsive chloride pump proteins provided herein can comprise a light-responsive protein expressed on the cell membrane, wherein the protein comprises a core amino acid sequence at least about 90%, 91%, 92%, 93%, 94%, 95%, 96%, 97%, 98%, 99%, or 100% identical to the sequence shown in SEQ ID NO: 1 and a trafficking signal (e.g., which can enhance transport of the light-responsive chloride pump protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker which can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV.

In some aspects, the light-responsive chloride pump protein can comprise a core amino acid sequence at least about 90%, 91%, 92%, 93%, 94%, 95%, 96%, 97%, 98%, 99%, or 100% identical to the sequence shown in SEQ ID NO: 1 and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the light-responsive chloride pump protein comprises an N-terminal signal peptide, a C-terminal ER Export signal, and a C-terminal trafficking signal. In some embodiments, the C-terminal ER Export signal and the C-terminal trafficking signal can be linked by a linker. The linker can comprise any of about 5, 10, 20, 30, 40, 50, 75, 100, 125, 150, 175, 200, 225, 250, 275, 300, 400, or 500 amino acids in length. The linker can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide comprises the amino acid sequence MTETLPPVTESAVALQAE. In another embodiment, the light-responsive chloride pump protein comprises an amino acid sequence at least 95% identical to SEQ ID NO:2.

Moreover, in other aspects, the light-responsive chloride pump proteins can comprise a core amino acid sequence at least about 90%, 91%, 92%, 93%, 94%, 95%, 96%, 97%, 98%, 99%, or 100% identical to the sequence shown in SEQ ID NO: 1, wherein the N-terminal signal peptide of SEQ ID NO:1 is deleted or substituted. In some embodiments, other signal peptides (such as signal peptides from other opsins) can be used. The light-responsive protein can further comprise an ER transport signal and/or a membrane trafficking signal described herein. In some embodiments, the light-responsive chloride pump protein comprises an amino acid sequence at least 95% identical to SEQ ID NO:3.

In some embodiments, the light-responsive opsin protein is a NpHR opsin protein comprising an amino acid sequence at least 95%, at least 96%, at least 97%, at least 98%, at least 99% or 100% identical to the sequence shown in SEQ ID NO:1. In some embodiments, the NpHR opsin protein further comprises an endoplasmic reticulum (ER) export signal and/or a membrane trafficking signal. For example, the NpHR opsin protein comprises an amino acid sequence at least 95% identical to the sequence shown in SEQ ID NO:1 and an endoplasmic reticulum (ER) export signal. In some embodiments, the amino acid sequence at least 95% identical to the sequence shown in SEQ ID NO:1 is linked to the ER export signal through a linker. In some embodiments, the ER export signal comprises the amino acid sequence FXYENE, where X can be any amino acid. In another embodiment, the ER export signal comprises the amino acid sequence VXXSL, where X can be any amino acid. In some embodiments, the ER export signal comprises the amino acid sequence FCYENEV. In some embodiments, the NpHR opsin protein comprises an amino acid sequence at least 95% identical to the sequence shown in SEQ ID NO:1, an ER export signal, and a membrane trafficking signal. In other embodiments, the NpHR opsin protein comprises, from the N-terminus to the C-terminus, the amino acid sequence at least 95% identical to the sequence shown in SEQ ID NO:1, the ER export signal, and the membrane trafficking signal. In other embodiments, the NpHR opsin protein comprises, from the N-terminus to the C-terminus, the amino acid sequence at least 95% identical to the sequence shown in SEQ ID NO:1, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence K S R I T S E G E Y I P L D Q I D I N V. In some embodiments, the membrane trafficking signal is linked to the amino acid sequence at least 95% identical to the sequence shown in SEQ ID NO:1 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-responsive opsin protein further comprises an N-terminal signal peptide. In some embodiments, the light-responsive opsin protein comprises the amino acid sequence of SEQ ID NO:2. In some embodiments, the light-responsive opsin protein comprises the amino acid sequence of SEQ ID NO:3.

Also provided herein are polynucleotides encoding any of the light-responsive chloride ion pump proteins described herein, such as a light-responsive protein comprising a core amino acid sequence at least about 90%, 91%, 92%, 93%, 94%, 95%, 96%, 97%, 98%, 99%, or 100% identical to the sequence shown in SEQ ID NO:1, an ER export signal, and a membrane trafficking signal. In another embodiment, the polynucleotides comprise a sequence which encodes an amino acid at least 95% identical to SEQ ID NO:2 and/or SEQ ID NO:3. The polynucleotides may be in an expression vector (such as, but not limited to, a viral vector described herein). The polynucleotides may be used for expression of the light-responsive chloride ion pump proteins in neurons of the central or peripheral nervous systems.

Further disclosure related to light-responsive chloride pump proteins can be found in U.S. Patent Application Publication Nos: 2009/0093403 and 2010/0145418 as well as in International Patent Application No: PCT/US2011/028893, the disclosures of each of which are hereby incorporated by reference in their entireties.

Light-Responsive Proton Pumps

In some aspects, the light-responsive opsin proteins described herein are light-responsive proton pumps. In some aspects of the compositions and methods provided herein, one or more light-responsive proton pumps are expressed on the plasma membranes of neurons of the central or peripheral nervous systems.

In some embodiments, the light-responsive proton pump protein can be responsive to blue light and can be derived from *Guillardia theta*, wherein the proton pump protein can be capable of mediating a hyperpolarizing current in the cell when the cell is illuminated with blue light. The light can have a wavelength between about 450 and about 495 nm or can have a wavelength of about 490 nm. In another embodiment, the light-responsive proton pump protein can comprise an amino acid sequence at least about 90%, 91%, 92%, 93%, 94%, 95%, 96%, 97%, 98%, 99%, or 100% identical to the sequence shown in SEQ ID NO:4. The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least about 90%, 91%, 92%, 93%, 94%, 95%, 96%, 97%, 98%, 99%, or 100% identical to the sequence shown in SEQ ID NO:4 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive proton pump proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4. The polynucleotides may be used for expression of the light-responsive proton pumps in neural cells of the central or peripheral nervous systems.

Further disclosure related to light-responsive proton pump proteins can be found in International Patent Application No. PCT/US2011/028893, the disclosure of which is hereby incorporated by reference in its entirety.

Light-Activated Cation Channel Proteins

In some aspects, the light-responsive opsin proteins described herein are light-activated cation channel proteins. In some aspects of the methods provided herein, one or more light-activated cation channels can be expressed on the plasma membranes of the neural cells of the central or peripheral nervous systems.

In some aspects, the light-activated cation channel protein can be derived from *Chlamydomonas reinhardtii*, wherein the cation channel protein can be capable of mediating a depolarizing current in the cell when the cell is illuminated with light. In another embodiment, the light-activated cation channel protein can comprise an amino acid sequence at least about 90%, 91%, 92%, 93%, 94%, 95%, 96%, 97%, 98%, 99%, or 100% identical to the sequence shown in SEQ ID NO:5. The light used to activate the light-activated cation channel protein derived from *Chlamydomonas reinhardtii* can have a wavelength between about 460 and about 495 nm or can have a wavelength of about 480 nm. Additionally, the light can have an intensity of at least about 100 Hz. In some embodiments, activation of the light-activated cation channel derived from *Chlamydomonas reinhardtii* with light having an intensity of 100 Hz can cause depolarization-induced synaptic depletion of the neurons expressing the light-activated cation channel. The light-activated cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-activated cation channel protein to regulate the polarization state of the plasma membrane of the cell.

Additionally, the light-activated cation channel protein can contain one or more conservative amino acid substitutions and/or one or more non-conservative amino acid substitutions. The light-activated proton pump protein comprising substitutions, deletions, and/or insertions introduced into the native amino acid sequence suitably retains the ability to depolarize the plasma membrane of a neuronal cell in response to light.

Further disclosure related to light-activated cation channel proteins can be found in U.S. Patent Application Publication No. 2007/0054319 and International Patent Application Publication Nos. WO 2009/131837 and WO 2007/024391, the disclosures of each of which are hereby incorporated by reference in their entireties.

Step Function Opsins and Stabilized Step Function Opsins

In other embodiments, the light-activated cation channel protein can be a step function opsin (SFO) protein or a stabilized step function opsin (SSFO) protein that can have specific amino acid substitutions at key positions throughout the retinal binding pocket of the protein. In some embodiments, the SFO protein can have a mutation at amino acid residue C128 of SEQ ID NO:5. In other embodiments, the SFO protein has a C128A mutation in SEQ ID NO:5. In other embodiments, the SFO protein has a C128S mutation in SEQ ID NO:5. In another embodiment, the SFO protein has a C128T mutation in SEQ ID NO:5. In some embodiments, the SFO protein can comprise an amino acid sequence at least about 90%, 91%, 92%, 93%, 94%, 95%, 96%, 97%, 98%, 99%, or 100% identical to the sequence shown in SEQ ID NO:6.

In some embodiments, the SSFO protein can have a mutation at amino acid residue D156 of SEQ ID NO:5. In other embodiments, the SSFO protein can have a mutation at both amino acid residues C128 and D156 of SEQ ID NO:5. In one embodiment, the SSFO protein has an C128S and a D156A mutation in SEQ ID NO:5. In another embodiment, the SSFO protein can comprise an amino acid sequence at least about 90%, 91%, 92%, 93%, 94%, 95%, 96%, 97%, 98%, 99%, or 100% identical to the sequence shown in SEQ ID NO:7.

In some embodiments the SFO or SSFO proteins provided herein can be capable of mediating a depolarizing current in the cell when the cell is illuminated with blue light. In other embodiments, the light can have a wavelength of about 445 nm. Additionally, the light can have an intensity of about 100 Hz. In some embodiments, activation of the SFO or SSFO protein with light having an intensity of 100 Hz can cause depolarization-induced synaptic depletion of the neurons expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970 and U.S. Provisional Patent Application Nos. 61/410,704 and 61/511,905, the disclosures of each of which are hereby incorporated by reference in their entireties.

C1V1 Chimeric Cation Channels

In other embodiments, the light-activated cation channel protein can be a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein can further comprise a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein can further comprise a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein can comprise an amino acid sequence at least about 90%, 91%, 92%, 93%, 94%, 95%, 96%, 97%, 98%, 99%, or 100% identical to the sequence shown in SEQ ID NO:8.

In some embodiments, the C1V1 protein can mediate a depolarizing current in the cell when the cell is illuminated with green light. In other embodiments, the light can have a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, the light can have an intensity of about 100 Hz. In some embodiments, activation of the C1V1 chimeric protein with light having an intensity of 100 Hz can cause depolarization-induced synaptic depletion of the neurons expressing the C1V1 chimeric protein. In some embodiments, the disclosed C1V1 chimeric protein can have specific properties and characteristics for use in depolarizing the membrane of a neuronal cell in response to light.

C1V1 Chimeric Mutant Variants

In some aspects, the invention can include polypeptides comprising substituted or mutated amino acid sequences, wherein the mutant polypeptide retains the characteristic light-responsive nature of the precursor C1V1 chimeric polypeptide but may also possess altered properties in some specific aspects. For example, the mutant light-activated C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-activated cation channels, and/or strong expression in animal cells.

Accordingly, provided herein are C1V1 chimeric light-activated proteins that can have specific amino acid substitutions at key positions throughout the retinal binding pocket of the VChR1 portion of the chimeric polypeptide. In some embodiments, the C1V1 protein can have a mutation at amino acid residue E122 of SEQ ID NO:7. In some embodiments, the C1V1 protein can have a mutation at amino acid residue E162 of SEQ ID NO:7. In other embodiments, the C1V1 protein can have a mutation at both amino acid residues E162 and E122 of SEQ ID NO:7. In other embodiments, the C1V1 protein can comprise an amino acid sequence at least about 90%, 91%, 92%, 93%, 94%, 95%, 96%, 97%, 98%, 99%, or 100% identical to the sequence shown in SEQ ID NO:9, SEQ ID NO:10, or SEQ ID NO:11. In some embodiments, each of the disclosed mutant C1V1 chimeric proteins can have specific properties and characteristics for use in depolarizing the membrane of an animal cell in response to light.

In some aspects, the C1V1-E122 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In other embodiments, the C1V1-E122 mutant chimeric protein can mediate a depolarizing current in the cell when the cell is illuminated with red light. In some embodiments, the red light can have a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E122 mutant chimeric protein with light having an intensity of 100 Hz can cause depolarization-induced synaptic depletion of the neurons expressing the C1V1-E122 mutant chimeric protein. In some embodiments, the disclosed C1V1-E122 mutant chimeric protein can have specific properties and characteristics for use in depolarizing the membrane of a neuronal cell in response to light.

In other aspects, the C1V1-E162 mutant chimeric protein is capable of mediating a depolarizing current in the cell when the cell is illuminated with light. In some embodiments the light can be green light. In other embodiments, the light can have a wavelength of between about 540 nm to about 535 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, the light can have an intensity of about 100 Hz. In some embodiments, activation of the C1V1-E162 mutant chimeric protein with light having an intensity of 100 Hz can cause depolarization-induced synaptic depletion of the neurons expressing the C1V1-E162 mutant chimeric protein. In some embodiments, the disclosed C1V1-E162 mutant chimeric protein can have specific properties and characteristics for use in depolarizing the membrane of a neuronal cell in response to light.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-activated cation channel proteins. Additionally, the light can have an intensity of about 100 Hz. In some embodiments, activation of the C1V1-E122/E162 mutant chimeric protein with light having an intensity of 100 Hz can cause depolarization-induced synaptic depletion of the neurons expressing the C1V1-E122/E162 mutant chimeric protein. In some embodiments, the disclosed C1V1-E122/E162 mutant chimeric protein can have specific properties and characteristics for use in depolarizing the membrane of a neuronal cell in response to light.

Further disclosure related to C1V1 chimeric cation channels as well as mutant variants of the same can be found in U.S. Provisional Patent Application Nos. 61/410,736, 61/410,744, and 61/511,912, the disclosures of each of which are hereby incorporated by reference in their entireties.

Polynucleotides

The disclosure also provides polynucleotides comprising a nucleotide sequence encoding a light-responsive opsin protein described herein. In some embodiments, the polynucleotide comprises an expression cassette. In some embodiments, the polynucleotide is a vector comprising the above-described nucleic acid(s). In some embodiments, the nucleic acid encoding a light-activated protein of the disclosure is operably linked to a promoter. Promoters are well known in the art. Any promoter that functions in the host cell can be used for expression of the light-responsive opsin proteins and/or any variant thereof of the present disclosure. In one embodiment, the promoter used to drive expression of the light-responsive opsin proteins is a promoter that is specific to motor neurons. In another embodiment, the promoter used to drive expression of the light-responsive opsin proteins is a promoter that is specific to central nervous system neurons. In other embodiments, the promoter is capable of driving expression of the light-responsive opsin proteins in neurons of both the sympathetic and/or the parasympathetic nervous systems. Initiation control regions or promoters, which are useful to drive expression of the light-responsive opsin proteins or variant thereof in a specific animal cell are numerous and familiar to those skilled in the art. Virtually any promoter capable of driving these nucleic acids can be used. Examples of motor neuron-specific genes can be found, for example, in Kudo, et al., Human Mol. Genetics, 2010, 19(16): 3233-3253, the contents of which are hereby incorporated by reference in their entirety. In some embodiments, the promoter used to drive expression of the light-activated protein can be the Thy1 promoter, which is capable of driving robust expression of transgenes in neurons of both the central and peripheral nervous systems (See, e.g., Llewellyn, et al., 2010, Nat. Med., 16(10):1161-1166). In other embodiments, the promoter used to drive expression of the light-responsive opsin protein can be the EF1α promoter, a cytomegalovirus (CMV) promoter, the CAG promoter, the sinapsin promoter, or any other ubiquitous promoter capable of driving expression of the light-responsive opsin proteins in the peripheral and/or central nervous system neurons of mammals.

Also provided herein are vectors comprising a nucleotide sequence encoding a light-responsive opsin protein or any variant thereof described herein. The vectors that can be administered according to the present invention also include vectors comprising a nucleotide sequence which encodes an RNA (e.g., an mRNA) that when transcribed from the polynucleotides of the vector will result in the accumulation of light-responsive opsin proteins on the plasma membranes of target animal cells. Vectors which may be used, include, without limitation, lentiviral, HSV, adenoviral, and andeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, the vector is a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (See, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" in *Parvoviruses* (J R Kerr, S F Cotmore. M E Bloom, R M Linden, C R Parrish, Eds.) p 5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and International Patent Application Publication No.: WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: WO 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (UR) regions, and a plasmid carrying the AAV encapsidation genes (rep and cap genes), into a cell line that is infected with a human helper virus (for example, an adenovirus). The AAV recombinants that are produced are then purified by standard techniques.

In some embodiments, the vector(s) for use in the methods of the invention are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the invention includes a recombinant virus particle (recombinant because it contains a recombinant polynucleotide) comprising any of the vectors described herein. Methods of producing such particles are known in the art and are described in U.S. Pat. No. 6,596, 535, the disclosure of which is hereby incorporated by reference in its entirety.

Delivery of Light-Responsive Opsin Proteins and Lanthanide-Doped Nanoparticles

In some aspects, polynucleotides encoding the light-responsive opsin proteins disclosed herein (for example, an AAV1 vector) can be delivered to neurons of the central or peripheral nervous system with a needle, catheter, or related device, using neurosurgical techniques known in the art, such as by stereotactic injection (See, e.g., Stein et al., *J. Virol.*, 1999, 73:34243429; Davidson et al., *Proc. Nat. Acad. Sci. U.S.A.*, 2000, 97:3428-3432; Davidson et al., *Nat. Genet.*, 1993, 3:219-223; and Alisky & Davidson, *Hum. Gene Ther.*, 2000, 11:2315-2329, the contents of each of which are hereby incorporated by reference herein in their entireties) or fluoroscopy. In some embodiments, the polynucleotide encoding the light-responsive opsin proteins disclosed herein (for example, an AAV1 vector) can be delivered to neurons of the peripheral nervous system by injection into any one of the spinal nerves (such as the cervical spinal nerves, the thoracic spinal nerves, the lumbar spinal nerves, the sacral spinal nerves, and/or the coccygeal spinal nerves).

Other methods to deliver the light-responsive opsin proteins to the nerves of interest can also be used, such as, but not limited to, transfection with ionic lipids or polymers, electroporation, optical transfection, impalefection, or via gene gun.

In another aspect, the polynucleotide encoding the light-responsive opsin proteins disclosed herein (for example, an AAV2 vector) can be delivered directly to muscles innervated by the neurons of the peripheral nervous system. Because of the limitations inherent in injecting viral vectors directly into the specific cell bodies which innvervate particular muscles, researchers have attempted to deliver transgenes to peripheral neurons by injecting viral vectors directly into muscle. These experiments have shown that some viral serotypes such as adenovirus, AAV2, and Rabies glycoprotein-pseudotyped lentivirus can be taken up by muscle cells and retrogradely transported to motor neurons across the neuromuscular synapse (See, e.g., Azzouz et al., 2009, *Antioxid Redox Signal.*, 11(7):1523-34; Kaspar et al., 2003, *Science*, 301(5634):839-842; Manabe et al., 2002, *Apoptosis*, 7(4):329-334, the disclosures of each of which are herein incorporated by reference in their entireties).

Accordingly, in some embodiments, the vectors expressing the light-responsive opsin proteins disclosed herein (for example, an AAV2 vector) can be delivered to the neurons responsible for the innervation of muscles by direct injection into the muscle of interest.

The lanthanide-doped nanoparticles disclosed herein can be delivered to neurons expressing one or more light-responsive opsin proteins by any route, such as intravascularly, intracranially, intracerebrally, intramuscularly, intradermally, intravenously, intraocularly, orally, nasally, topically, or by open surgical procedure, depending upon the anatomical site or sites to which the nanoparticles are to be delivered. The nanoparticles can additionally be delivered by the same route used for delivery of the polynucleotide vectors expressing the light-responsive opsin proteins, such as any of those described above. The nanoparticles can also be administered in an open manner, as in the heart during open heart surgery, or in the brain during stereotactic surgery, or by intravascular interventional methods using catheters going to the blood supply of specific organs, or by other interventional methods.

Pharmaceutical compositions used for the delivery and/or storage of polynucleotides encoding the light-responsive opsin proteins disclosed herein and/or the lanthanide-doped nanoparticles disclosed herein can be formulated according to known methods for preparing pharmaceutically useful compositions. Formulations are described in a number of sources which are well known and readily available to those skilled in the art. For example, Remington's *Pharmaceutical Sciences* (Martin E W, 1995, Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze dried (lyophilized) condition requiring only the condition of the sterile liquid carrier, for example, water for injections, prior to use.

The lanthanide-doped nanoparticles may also be administered intravenously or intraperitoneally by infusion or injection. Solutions of the nanoparticles and/or cells can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion of the lanthanide-doped nanoparticles described herein can include sterile aqueous solutions or dispersions or sterile powders comprising the active ingredient which are adapted for the extemporaneous preparation of sterile injectable or infusible solutions or dispersions. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thimerosal, and the like.

Sources of Infrared or Near Infrared Electromagnetic Radiation

Any device that is capable of producing a source of electromagnetic radiation having a wavelength in the infrared (IR) or near infrared (NIR) spectrum may be used to activate one or more light-responsive proteins expressed on the surface of a neuron in combination with the lanthanide-doped nanoparticles described herein. The IR or NIR source can be configured to provide optical stimulus to a specific target region of the brain. The IR or NIR source can additionally provide continuous IR or NIR electromagnetic radiation and/or pulsed IR or NIR electromagnetic radiation, and may be programmable to provide IR or NIR electromagnetic radiation in pre-determined pulse sequences.

In other aspects, the implantable IR or NIR source does not require physical tethering to an external power source. In some embodiments, the power source can be an internal battery for powering the IR or NIR source. In another embodiment, the implantable IR or NIR source can comprise an external antenna for receiving wirelessly transmitted electromagnetic energy from an external power source for powering the IR or NIR source. The wirelessly transmitted electromagnetic energy can be a radio wave, a microwave, or any other electromagnetic energy source that can be transmitted from an external source to power the IR or NIR-generating source. In one embodiment, the IR or NIR source is controlled by an integrated circuit produced using semiconductor or other processes known in the art.

In some aspects, the implantable IR or NIR electromagnetic radiation source can be externally activated by an external controller. The external controller can comprise a power generator which can be mounted to a transmitting coil. In some embodiments of the external controller, a battery can be connected to the power generator, for providing power thereto. A switch can be connected to the power generator, allowing an individual to manually activate or deactivate the power generator. In some embodiments, upon activation of the switch, the power generator can provide power to the IR or NIR electromagnetic radiation source through electromagnetic coupling between the transmitting coil on the external controller and the external antenna of the implantable IR or NIR source. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver or a biomedical telemetry system (See, e.g., Kiourti, "Biomedical Telemetry: Communication between Implanted Devices and the External World, *Opticon*1826, (8): Spring, 2010).

In some aspects, the intensity of the IR or NIR electromagnetic radiation reaching the neural cells (such as neural cells expressing one or more light-responsive opsin proteins) produced by the IR or NIR electromagnetic radiation source has an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers.

In other aspects, the IR or NIR electromagnetic radiation produced by the IR or NIR electromagnetic radiation source can have a wavelength encompassing the entire infrared spectrum, such as from about 740 nm to about 300,000 nm. In other embodiments, the IR or NIR electromagnetic radiation produced by the IR or NIR electromagnetic radiation source can have a wavelength corresponding to the NIR spectrum, such as about 740 nm to about 1400 nm. In other embodiments, NIR electromagnetic radiation produced has a wavelength between 700 nm and 1000 nm.

In some aspects, an IR or NIR electromagnetic radiation source is used to hyperpolarize or depolarize the plasma membranes of neural cells (such as neural cells expressing one or more light-responsive opsin proteins) in the brain or central nervous system of an individual when used in combination with the lanthanide-doped nanoparticles disclosed herein. In some embodiments, the skull of the individual is surgically thinned in an area adjacent to the brain region of interest without puncturing the bone. The IR or NIR electromagnetic radiation source can then be placed directly over the thinned-skull region. In other embodiments, the IR or NIR electromagnetic radiation generator is implanted under the skin of the individual directly adjacent to the thinned skull region.

In some aspects, an IR or NIR electromagnetic radiation source is used to hyperpolarize or depolarize the plasma membranes of neural cells (such as neural cells expressing one or more light-responsive opsin proteins) in the peripheral nervous system of an individual when used in combination with the lanthanide-doped nanoparticles disclosed herein. In some embodiments, the IR or NIR electromagnetic radiation source is surgically implanted under the skin of the individual directly adjacent to the peripheral neural cell of interest. In other embodiments, the IR or NIR electromagnetic radiation source is placed against the skin directly adjacent to the peripheral neural cell of interest. In one embodiment, the IR or NIR electromagnetic radiation source is held against the skin in a bracelet or cuff configuration.

Examples of the IR or NIR electromagnetic radiation sources, particularly those small enough to be implanted under the skin, can be found in U.S. Patent Application Publication Nos.: 2009/0143842, 2011/0152969, 2011/0144749, and 2011/0054305, the disclosures of each of which are incorporated by reference herein in their entireties.

In still other aspects, the lanthanide-doped nanoparticles disclosed herein can be exposed to higher wavelength light in the visible spectrum (such as red light) to upconvert the higher wavelength visible light into lower wavelength visible light (such as blue or green light). As described above, light passes through biological tissue poorly. However, when visible light does penetrate into tissues, it typically does so in higher wavelengths which correspond to red light (for example, between about 620 nm to 740 nm). Accordingly, the lanthanide-doped nanoparticles disclosed herein can additionally be used in combination with optical sources of visible light to upshift wavelengths corresponding to red light into wavelengths corresponding to green or blue light (for example, between about 440 nm and 570 nm). Examples of light stimulation devices, including light sources, can be found in International Patent Application Nos.: PCT/US08/50628 and PCT/US09/49936 and in Llewellyn et al., 2010, *Nat. Med.*, 16(10):161-165, the disclosures of each of which are hereby incorporated herein in their entireties.

Methods of the Invention

Depolarization of Neural Cells

Provided herein are methods to depolarize the plasma membrane of a neural cell in an individual comprising placing a plurality of lanthanide-doped nanoparticles in proximity to the neural cell; and exposing the plurality of nanoparticles to electromagnetic radiation in the infrared (IR) or near infrared (NIR) spectrum, wherein the electromagnetic radiation in the IR or NIR spectrum is upconverted into light in the visible spectrum by the nanoparticles, and wherein a light-responsive opsin is expressed on the plasma membrane of the neural cells and activation of the opsin by the light in the visible spectrum induces the depolarization of the plasma membrane.

Also provided herein is a method to depolarize the plasma membrane of a neural cell in an individual comprising administering a polynucleotide encoding a light-responsive opsin to a neural cell in the brain of an individual, wherein the light-responsive protein is expressed on the plasma membrane of the neural cell and the opsin is capable of inducing membrane depolarization of the neural cell when illuminated with light administering a plurality of lanthanide-doped nanoparticles in proximity to the neural cell; and exposing the plurality of nanoparticles to electromagnetic radiation in the infrared (IR) or near (IR) spectrum, wherein the electromagnetic radiation in the IR or near IR spectrum is upconverted into light in the visible spectrum and the activation of the opsin by the light in the visible spectrum induces the depolarization of the plasma membrane.

In some embodiments, the light-responsive opsin protein is ChR2, VChR1, or C1V1. In other embodiments, the light-responsive opsin protein is selected from the group consisting of SFO, SSFO, C1V1-E122, C1V1-E162, and C1V1-E122/E162.

The lanthanide metal can be ions or atoms from any of the lanthanide series of elements, such as Lanthanum, Cerium, Praseodymium, Neodymium, Promethium, Samarium, Europium, Gadolinium, Terbium, Dysprosium, Holmium, Erbium, Thulium, Ytterbium, or Lutetium. In other embodiments, the nanoparticles comprise $NaYF_4:Yb/X/Gd$, wherein X is Er, Tm, or Er/Tm.

The electromagnetic radiation in the IR or near IR spectrum can be upconverted into light having a wavelength of about 450 nm to about 550 nm. The light can have wavelengths corresponding to red, yellow, amber, orange, green, or blue light. In some embodiments, the individual is a human or a non-human animal. In other embodiments, the neural cell is in the peripheral nervous system. In another embodiment, the neural cell is in the central nervous system.

Hyperpolarization of Neural Cells

Provided herein are methods to hyperpolarize the plasma membrane of a neural cell in an individual comprising placing a plurality of lanthanide-doped nanoparticles in proximity to the neural cell; and exposing the plurality of nanoparticles to electromagnetic radiation in the infrared (IR) or near infrared (NIR) spectrum, wherein the electromagnetic radiation in the IR or NIR spectrum is upconverted into light in the visible spectrum by the nanoparticles, and wherein a light-responsive opsin is expressed on the plasma membrane of the neural cells and activation of the opsin by the light in the visible spectrum induces the hyperpolarization of the plasma membrane.

Also provided herein is a method to hyperpolarize the plasma membrane of a neural cell in an individual comprising administering a polynucleotide encoding a light-responsive opsin to a neural cell in the brain of an individual, wherein the light-responsive protein is expressed on the plasma membrane of the neural cell and the opsin is capable of inducing membrane depolarization of the neural cell when illuminated with light administering a plurality of lanthanide-doped nanoparticles in proximity to the neural cell; and exposing the plurality of nanoparticles to electromagnetic radiation in the infrared (IR) or near (IR) spectrum, wherein the electromagnetic radiation in the IR or near IR spectrum is upconverted into light in the visible spectrum and the activation of the opsin by the light in the visible spectrum induces the hyperpolarization of the plasma membrane.

In some embodiments, the light-responsive opsin protein is an NpHR or a GtR3.

The lanthanide metal can be ions or atoms from any of the lanthanide series of elements, such as Lanthanum, Cerium, Praseodymium, Neodymium, Promethium, Samarium, Europium, Gadolinium, Terbium, Dysprosium, Holmium, Erbium, Thulium, Ytterbium, or Lutetium. In other embodiments, the nanoparticles comprise $NaYF_4:Yb/X/Gd$, wherein X is Er, Tm, or Er/Tm.

The electromagnetic radiation in the IR or near IR spectrum can be upconverted into light having a wavelength of about 450 nm to about 550 nm. The light can have wavelengths corresponding to red, yellow, amber, orange, green, or blue light. In some embodiments, the individual is a human or a non-human animal. In other embodiments, the neural cell is in the peripheral nervous system. In another embodiment, the neural cell is in the central nervous system.

Kits

Also provided herein are kits comprising polynucleotides encoding a light-responsive opsin protein (such as any of the light-responsive opsin proteins described herein) and lanthanide-doped nanoparticles for use in any of the methods disclosed herein to alter the membrane polarization state of one or more neurons of the central and/or peripheral nervous system. In some embodiments, the kits further comprise an infrared or near infrared electromagnetic radiation source. In other embodiments, the kits further comprise instructions for using the polynucleotides and lanthanide-doped nanoparticles described herein. In still other embodiments, the lanthanide-doped nanoparticles described herein are embedded and/or trapped in a biocompatible material (such as any of the biocompatible materials described above).

Exemplary Embodiments

Aspects of the present disclosure may be more completely understood in consideration of the detailed description of various embodiments of the present disclosure that follows in connection with the accompanying drawings. This description and the various embodiments are presented as follows:

The embodiments and specific applications discussed herein may be implemented in connection with one or more of the above-described aspects, embodiments and implementations, as well as with those shown in the figures and described below. Reference may also be made to Wang et al., 2010, *Nature,* 463(7284):1061-5, which is fully incorporated herein by reference. For further details on light responsive molecules and/or opsins, including methodology, devices and substances, reference may also be made to the following background publications: U.S. Patent Publication No. 2010/0190229, entitled "System for Optical Stimulation of Target Cells" to Zhang et al.; U.S. Patent Publication No. 2007/0261127, entitled "System for Optical Stimulation of Target Cells" to Boyden et al. These applications form part of the provisional patent document and are fully-incorporated herein by reference. Consistent with these publications, numerous opsins can be used in mammalian cells in vivo and in vitro to provide optical stimulation and control of target cells. For example, when ChR2 is introduced into an electrically-excitable cell, such as a neuron, light activation of the ChR2 channelrhodopsin can result in excitation and/or firing of the cell. In instances when NpHR is introduced into an electrically-excitable cell, such as a neuron, light activation of the NpHR opsin can result in inhibition of firing of the cell. These and other aspects of the disclosures of the above-referenced patent applications may be useful in implementing various aspects of the present disclosure.

In various embodiments of the present disclosure, minimally invasive delivery of light, for example as can be useful for manipulation of neural circuits with optogenetics, using near infrared up-conversion nanocrystals, is achieved. This is used to avoid the implantation of light sources within living tissues, including, for example, a subject's brain. Mammalian tissue has a transparency window in near infrared part of the spectrum (700-1000 nm). Accordingly, aspects of the present disclosure relate to the use of nanoparticles for the purpose of using (near) infrared light to deliver energy into the depth of a brain by converting the infrared light into visible wavelengths at a site of interest.

In certain embodiments, delivering visible wavelengths at a site of interest within the brain is achieved through a process of optical upconversion in Lanthanide-doped nanocrystals. During upconversion 3-4 photons are absorbed by the material which then emits one photon with the energy ~1.5-2 times the energy of absorbed photons. For example NaYF4:Yb/X/Gd nanocrystals can absorb 980 nm light and emit light with spectra centered between 450-550 nm depending on the nature and relative content of dopants (X=Er, Tm, Er/Tm). For more information regarding modifying the light emitted from the nanoparticles, see Wang et al., *Nature,* 2010, 463(7284):1061-5, the disclosure of which is incorporated by reference herein in its entirety.

In certain embodiments a single step surgery is performed to modify a target cell population and provide nanoparticles to convert near infrared light to visible light that stimulates the modified target cell population. During the surgery, the surgeon injects both an adeno-associated virus carrying an opsin gene and a nanoparticle solution to a site of interest. The virus is optimized to only infect the target cell population. Similarly, the nanoparticles are functionalized with antibodies so that the nanoparticles anchor to the target cell population as well. In certain more specific embodiments the target cell population is a particular neuron type. After surgery is completed, a LED that emits near infrared light is placed on a thinned portion of the patient's skull, underneath the skin. A battery can also be implanted underneath the skin to power the LED. In certain embodiments the battery has characteristics similar to those of a pacemaker battery. A microcontroller can be used to control the battery to deliver energy to the LED at specified intervals, resulting in LED light pulses at specified intervals.

Certain aspects of the present disclosure are directed to the use of optogenetics in vivo. Optogenetics, applied in vivo, relies on light delivery to specific neuron populations that can be located deep within the brain. Mammalian tissue is highly absorptive and scatters light in the visible spectrum. However, near infrared light is able to penetrate to deep levels of the brain without excessive absorption or scattering.

Certain aspects of the present disclosure are directed to imbedding nanoparticles in the brain near target neurons. The nanoparticles can be lanthanide doped-nanoparticle. Nanoparticles doped with Lanthanides or with other dopants can be optimized with respect to a particular opsin's activation spectra. As discussed in more detail in Wang et al., *Nature,* 2010, 463(7284):1061-5, the disclosure of which is incorporated by reference herein in its entirety, the spectra of the light emitted from lanthanide-doped nanocrystals can be manipulated based on which dopants are used, and how much. Similarly, the light emitted from nanoparticles doped with other molecules can be manipulated based on the concentration of dopants.

The ability to provide different output spectra depending on the doping of nanoparticles allows for a non-invasive approach to acute neural manipulation. A light source, such as a LED can be mounted onto a thinned skull under the skin. Depending on the composition of nanoparticles, and the opsin delivered to the target neurons, aspects of the present disclosure can be used for neural excitation or silencing. Similarly, multiple neural populations may be controlled simultaneously through the use of various dopants and opsins in combination.

Turning to FIG. 1, a patient's head 100 is shown. A target (neural) cell population 114 includes light responsive molecules. These light responsive molecules can include, but are not necessarily limited to, opsins derived from Channelrhodopsins (e.g. ChR1 or ChR2) or Halorhodopins (NpHR). The specific molecule can be tailored/selected based upon the desired effect on the target cell population and/or the wavelength at which the molecules respond to light.

Nanocrystals 110 are introduced near or at the target cell populate. Various embodiments of the present disclosure are directed toward methods and devices for positioning and maintaining positioning of the nanocrystals near the target cell population. Certain embodiments are directed toward anchoring the nanocrystals to cells of (or near) the target cell population using antibodies.

According to other example embodiments, a structure can be introduced that includes the nanocrystals. For instance, a mesh structure can be coated with the nanocrystals. The synthetic mesh can be constructed so as to allow the dendrites and axons to pass through the mess without allowing the entire neuron (e.g., the cell body) to pass. One example of such a mesh has pores that are on the order of 3-7 microns in diameter and is made from polyethylene terephthalate. This mesh structure can be constructed with light-responsive cells/neurons contained therein and/or be placed near the target cell population, which includes the light-responsive cells. Consistent with another embodiment, one or more transparent capsules, each containing a solution of nanocrystals, can be positioned near the target cell populations.

Embodiments of the present disclosure are also directed toward various optical sources of stimulation. These sources can include, but are not limited to, external laser sources and light-emitting diodes (LEDs). Particular aspects of the present disclosure are directed toward the relatively low absorption and/or scattering/diffusion caused by intervening material when the light is at certain wavelengths (e.g., (near) infrared). Accordingly, the light source can be externally located because of the ability to penetrate the tissue with little loss of optical intensity or power. Moreover, reduced diffusion can be particularly useful for providing a relatively-high spatial-precision for the delivery of the light. Thus, embodiments of the present disclosure are directed toward multiple target cell populations with respective nanocrystals that can be individually controlled using spatially-precise optical stimulus. For instance, the nanocrystals can be implanted in several locations within the brain. The light source can then be aimed at a respective and particular location. Multiple light sources can also be used for simultaneous stimulation of a plurality of locations.

Consistent with a particular embodiment of the present disclosure, the skull 102 has a thinned portion 106. An LED 104 is located above the thinned portion of the skull and emits near infrared light 108. When the IR hits nanocrystal 110, it is absorbed. The nanocrystal emits visible light 112 in response to absorbing the IR light 108. The visible light 112 is absorbed by modified cell 114.

The system shown in FIG. 1 allows for delivery of light to a target cell deep within a patient's brain tissue. The light responsive molecule can be specifically targeted to a neural cell type of interest. Similarly, the nanocrystals 112 are anchored to the neural cell with antibodies chosen based on the type of neural cell 114 being targeted.

Turning to FIG. 2, a group of neurons is illuminated with infrared light 208 between 700-1000 nm. Target neurons 214 express an opsin gene, allowing the neurons to be activated or inhibited, depending on which opsin, and what wavelength of light is absorbed by the neurons 214. The target neurons 214 can be interspersed between other neurons 216. As shown in inset 202, target neurons 214 are coated with upconverting nanoparticles 210 that are anchored to the neural membrane via antibodies. The nanoparticles 210 absorb IR photons and emit visible photons that are then absorbed by opsins triggering neural activation.

The system of FIG. 2 can be used with a variety of target neurons 214. The opsin gene 215 expressed in the target neurons 214 is modified based on the target neuron. Similarly, the antibodies used to anchor the nanoparticles 210 to the target neuron membranes are modified to attach to a specific membrane type. As shown in inset 202, the nanoparticles 210 are closely linked to the target neurons so that visible light photons emitted by the nanoparticles 210 are absorbed by the target neurons 214.

Figure 3:
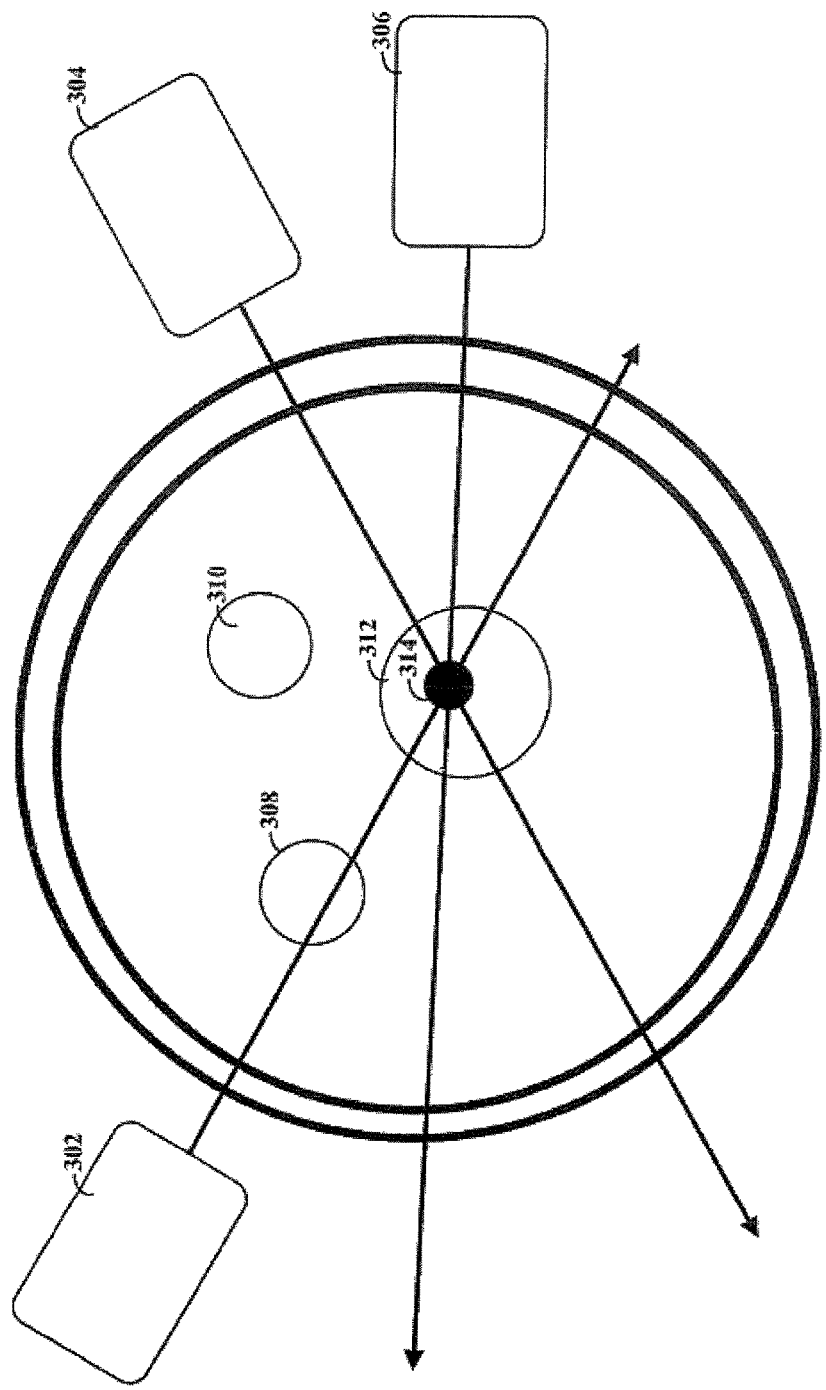
FIG. 3 depicts a system that uses multiple light sources, consistent with an embodiment of the present disclosure.

FIG. 3 depicts a system that uses multiple light sources, consistent with an embodiment of the present disclosure. A patient has nanoparticles located at target locations 308-312. The system includes light sources 302-306, which can be configured to generate light at a frequency that is upconverted by the nanoparticles located at target locations 308-312. Although three light sources are depicted, there can be any number of light sources. These light sources can be external to the patient (e.g., a targeting system that directs several light sources using mechanical positioning), using embedded lights sources (e.g., LEDs implanted on the skull) or combinations thereof. The target locations 308-312 include cells that have optically-responsive membrane molecules. These optically-responsive membrane molecules react to light at the upconverted frequency.

Nanoparticles located at the intersection 314 of the light from the different light sources 302-306 receive increased intensity of optical stimulus relative to other locations, including those locations within the path of light from a single light source. In this manner, the light intensity of each of the light sources can be set below a threshold level. When multiple light sources are directed at the same location, the threshold intensity level can be exceeded at the location. This allows for spatial control in three-dimensions and also allows for reduced inadvertent effects on non-targeted tissue. Consistent with one embodiment, the threshold level can be set according to an amount of light necessary to cause the desired effect (e.g., excitation or inhibition) on the target cells. Consistent with other embodiments, the threshold level can be set to avoid adverse effects on non-targeted tissue (e.g., heating).

The use of multiple light sources can also bring about a step-wise increase in light inntensity. For instance, a disease model could be tested by monitoring the effects of additional stimulation caused by the increase in light intensity. The use of independent light sources allows for relatively simple control over temporal and spatial increases or decreases. Consistent with other embodiments of the present disclosure, the spatial precision of the light sources can be varied between the different light sources. For example, a first light source can provide light that illuminates the entire target cell location. This allows for all cells within the population to be illuminated. A second light source can provide light having a focal point that illuminates less than all of the entire target cell location. The combination of the first and second (or more) light sources can be used to provide different levels of stimulation within the same cell population.

Embodiments of the present disclosure relate to the use of one or more light sources operating in a scanning mode. The light source(s) are aimed at specific locations within a target cell population. The effects of the stimulation can be monitored as the light source is used to scan or otherwise move within the target cell population. This can be particularly useful in connection with the three-dimensional control provided by the use of multiple light sources.

Various embodiments of the present disclosure are directed toward the use of nanocrystals that emit light at different wavelengths. This can be particularly useful when using multiple opsins having different light-absorption spectrums. The nanocrystals can be targeted toward different opsins and/or placed in the corresponding locations. While the present disclosure is amenable to various modifications and alternative forms, specifics thereof have been shown by way of example in the drawings and will be described in further detail. It should be understood that the intention is not to limit the disclosure to the particular embodiments and/or applications described. On the contrary, the intention is to cover all modifications, equivalents, and alternatives falling within the spirit and scope of the present disclosure.

EXAMPLES

Example 1: Use of Lanthanide-Doped Nanoparticles in the Use of Optogenetics to Hyperpolarize the Cholinergic Interneurons of the Nucleus Accumbens The nucleus accumbens (NAc) is a collection of neurons that forms the main part of the ventral striatum. The NAc is thought to play an important role in the complex mammalian behaviors associated with reward, pleasure, laughter, addiction, aggression, fear, and the placebo effect. Cholinergic interneurons within the NAc constitute less than 1% of the local neural population, yet they project throughout the NAc and provide its only known cholinergic input. In this Example, an optogenetic approach using a light-responsive chloride pump protein in combination with lanthanide-doped nanoparticles is used to block action potential firing in these cells, with both high temporal resolution and high cell-type specificity. To express microbial opsin genes specifically in cholinergic interneurons, a transgenic mouse line expressing Cre recombinase is employed under the choline acetyltransferase (ChAT) promoter. A Cre-inducible adeno-associated virus (AAV) vector carrying a yellow-light gated third-generation chloride pump halorhodopsin (eNpHR3.0) gene fused in-frame with coding sequence for enhanced yellow fluorescent protein (eYFP) is stereotactically injected.

Specifically, mice are anesthetized and then placed in a stereotactic head apparatus. Surgeries are performed on 4-6 week old mice and ophthalmic ointment is applied throughout to prevent the eyes from drying. A midline scalp incision is made followed by a craniotomy, and then AAV vector is injected with a 10 μl syringe and a 34 gauge metal needle. The injection volume and flow rate (1 μl at 0.15 μl/min) are controlled by an injection pump. Each NAc receives two injections (injection 1: AP 1.15 mm, ML 0.8 mm, DV −4.8 mm; injection 2: AP 1.15 mm, ML 0.8 mm, DV −4.2 mm). The virus injection and fiber position are chosen so that virtually the entire shell is stimulated.

Next, before withdrawing the needle, $NaYF_4$:Yb/Er/Gd, nanoparticles are injected into the Nac. Concentrations of 3.4, 8.5, or 17 nmoles of NaYF4:Yb/Er/Gd, nanoparticles are used. After injection of both the AAV vector and the lanthanide-doped nanoparticles is complete, the needle is left in place for 5 additional minutes and then very slowly withdrawn.

Following a recovery period, the mice are again anesthetized, the skulls of the mice are thinned and an NIR source of electromagnetic radiation is placed adjacent to the thinned skull-region. Simultaneous NIR stimulation and extracellular electrical recording are performed based on methods described previously using optical stimulation (Gradinaru et al., *J. Neurosci.*, 27, 14231-14238 (2007)). The electrode consists of a tungsten electrode (1 MΩ; 0.005 in; parylene insulation) with the tip of the electrode projecting beyond the fiber by 300-500 μm. The electrode is lowered through the NAc in approximately 100 μm increments, and NIR-upconverted optical responses are recorded at each increment. Signals are amplified and band-pass filtered (300 Hz low cut-off, 10 kHz high cut-off) before digitizing and recording to disk. At each site, 5 stimulation repetitions are presented and saved.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method to depolarize the plasma membrane of a neural cell in an individual comprising:
   (a) placing a plurality of lanthanide-doped nanoparticles in proximity to the neural cell, wherein the nanoparticles comprise $NaYF_4$:Yb/X/Gd, wherein X is Erbium (Er), Thulium (Tm), or Er/Tm, and wherein the nanoparticles comprise an antibody or fragment thereof; and
   (b) exposing the plurality of nanoparticles to electromagnetic radiation in the infrared (IR) or near infrared (NIR) spectrum, wherein the electromagnetic radiation in the IR or NIR spectrum is upconverted into light in the visible spectrum by the nanoparticles, and wherein a light-responsive opsin is expressed on the plasma membrane of the neural cell and activation of the opsin by the light in the visible spectrum induces the depolarization of the plasma membrane.

2. The method of claim 1, wherein the light-responsive opsin comprises an amino acid sequence having at least 85% amino acid sequence identity to SEQ ID NO:5 or 8.

3. The method of claim 1, wherein the light-responsive opsin comprises an amino acid sequence having at least 85% amino acid sequence identity to SEQ ID NO:6, 7, 9, 10, or 11.

4. The method of claim 1, wherein the electromagnetic radiation in the IR or NIR spectrum is upconverted into light having a wavelength of about 450 nm to about 550 nm.

5. The method of claim 1, wherein the electromagnetic energy in the IR or NIR spectrum is upconverted into light having a wavelength corresponding to red, yellow, amber light, green light, or blue light.

6. The method of claim 1, wherein the individual is:
   (a) a non-human animal; or
   (b) a human.

7. The method of claim 1, wherein the neural cell is a neural cell in the central nervous system; or in the peripheral nervous system.

8. The method of claim 1, wherein the antibody or fragment thereof is conjugated to the nanoparticle.

9. The method of claim 1, wherein the antibody or fragment thereof specifically targets the neural cell.

10. A method to depolarize the plasma membrane of a neural cell in an individual comprising:
    (a) administering a polynucleotide encoding a light-responsive opsin to an individual, wherein the light-responsive protein is expressed on the plasma membrane of a neural cell in the individual and the opsin is capable of inducing membrane depolarization of the neural cell when illuminated with light;
    (b) administering a plurality of lanthanide-doped nanoparticles in proximity to the neural cell, wherein the nanoparticles comprise $NaYF_4$:Yb/X/Gd, wherein X is Erbium (Er), Thulium (Tm), or Er/Tm, and wherein the nanoparticles comprise an antibody or fragment thereof; and
    (c) exposing the plurality of nanoparticles to electromagnetic radiation in the infrared (IR) or near infrared (NIR) spectrum, wherein the electromagnetic radiation in the IR or NIR spectrum is upconverted into light in the visible spectrum and the activation of the opsin by the light in the visible spectrum induces the depolarization of the plasma membrane.

11. The method of claim 10, wherein the light-responsive protein comprises an amino acid sequence having at least 85% amino acid sequence identity to SEQ ID NO:5, 6, 7, 8, 9, 10, or 11.

12. The method of claim 10, wherein the antibody or fragment thereof is conjugated to the nanoparticle.

13. The method of claim 10, wherein the antibody or fragment thereof specifically targets the neural cell.

14. A method to hyperpolarize the plasma membrane of a neural cell in an individual comprising:
    (a) placing a plurality of lanthanide-doped nanoparticles in proximity to the neural cell, wherein the nanoparticles comprise $NaYF_4$:Yb/X/Gd, wherein X is erbium (Er), thulium (Tm), or Er/Tm, and wherein the nanoparticles comprise an antibody or fragment thereof; and
    (b) exposing the plurality of nanoparticles to electromagnetic radiation in the infrared (IR) or near infrared (NIR) spectrum, wherein the electromagnetic radiation in the IR or NIR spectrum is upconverted into light in the visible spectrum by the nanoparticles, and wherein a light-responsive opsin is expressed on the plasma membrane and activation of the opsin by the light in the visible spectrum induces the hyperpolarization of the plasma membrane.

15. The method of claim 14, wherein the light-responsive opsin comprises an amino acid sequence having at least 85% amino acid sequence identity to SEQ ID NO:1 or SEQ ID NO:4.

16. The method of claim 14, wherein the electromagnetic energy in the IR or NIR spectrum is upconverted into light having a wavelength of about 450 nm to about 550 nm.

17. The method of claim 14, wherein the electromagnetic energy in the IR or NIR spectrum is upconverted into light having a wavelength corresponding to red, yellow, amber light, green light, or blue light.

18. The method of claim 14, wherein the individual is:
(a) a non-human animal; or
(b) a human.

19. The method of claim 14, wherein the neural cell is a neural cell in the:
(a) central nervous system; or
(b) peripheral nervous system.

20. The method of claim 14, wherein the antibody or fragment thereof is conjugated to the nanoparticle.

21. The method of claim 14, wherein the antibody or fragment thereof specifically targets the neural cell.

22. A method to hyperpolarize the plasma membrane of a neural cell in an individual comprising:
(a) administering a polynucleotide encoding a light-responsive opsin to an individual, wherein the light-responsive protein is expressed on the plasma membrane of a neural cell in the individual and the opsin is capable of inducing membrane hyperpolarization of the neural cell when illuminated with light;
(b) administering a plurality of lanthanide-doped nanoparticles in proximity to the neural cell, wherein the nanoparticles comprise $NaYF_4$:Yb/X/Gd, wherein X is Erbium (Er), Thulium (Tm), or Er/Tm, and wherein the nanoparticles comprise an antibody or fragment thereof; and
(c) exposing the plurality of nanoparticles to electromagnetic radiation in the infrared (IR) or near infrared (NIR) spectrum, wherein the electromagnetic radiation in the IR or NIR spectrum is upconverted into light in the visible spectrum and the activation of the opsin by the light in the visible spectrum induces the hyperpolarization of the plasma membrane.

23. The method of claim 22, wherein the light-responsive opsin comprises an amino acid sequence having at least 85% amino acid sequence identity to SEQ ID NO:1 or SEQ ID NO:4.

24. The method of claim 22, wherein the antibody or fragment thereof is conjugated to the nanoparticle.

25. The method of claim 22, wherein the antibody or fragment thereof specifically targets the neural cell.

26. A system comprising:
a) lanthanide-doped nanoparticles comprising $NaYF_4$:Yb/X/Gd, wherein X is Erbium (Er), Thulium (Tm), or Er/Tm, and wherein the nanoparticles further comprise an antibody or fragment thereof;
b) a nucleic acid comprising a nucleotide sequence encoding a light-responsive polypeptide; and
c) a source of infrared or near infrared electromagnetic radiation.

27. The system of claim 26, wherein the antibody or fragment thereof is conjugated to the nanoparticle.

28. The system of claim 26, wherein the antibody or fragment thereof specifically targets a neural cell.

* * * * *